US008007281B2

(12) United States Patent
Toly

(10) Patent No.: US 8,007,281 B2
(45) Date of Patent: Aug. 30, 2011

(54) LAPAROSCOPIC AND ENDOSCOPIC TRAINER INCLUDING A DIGITAL CAMERA WITH MULTIPLE CAMERA ANGLES

(76) Inventor: Christopher C. Toly, Seattle, WA (US)

( * ) Notice: Subject to any disclaimer, the term of this patent is extended or adjusted under 35 U.S.C. 154(b) by 1465 days.

(21) Appl. No.: 11/404,061

(22) Filed: Apr. 13, 2006

(65) Prior Publication Data

US 2006/0232664 A1   Oct. 19, 2006

Related U.S. Application Data

(63) Continuation-in-part of application No. 10/672,274, filed on Sep. 24, 2003, now Pat. No. 7,594,815.

(60) Provisional application No. 60/671,834, filed on Apr. 14, 2005.

(51) Int. Cl.
*G09B 23/28* (2006.01)

(52) U.S. Cl. ........................ 434/262; 600/112

(58) Field of Classification Search .................. 434/262; 345/157
See application file for complete search history.

(56) References Cited

U.S. PATENT DOCUMENTS

| | | | |
|---|---|---|---|
| 4,134,218 A | 1/1979 | Adams et al. | 35/16 |
| 4,273,682 A | 6/1981 | Kanomori | 252/511 |
| 4,360,345 A | 11/1982 | Hon | 434/262 |
| 4,872,841 A | 10/1989 | Hamilton et al. | 434/274 |
| 4,898,173 A | 2/1990 | Daglow et al. | 128/419 |
| 4,907,973 A | 3/1990 | Hon | 434/262 |
| 5,149,270 A | 9/1992 | McKeown | 434/262 |
| 5,205,286 A | 4/1993 | Soukup et al. | 128/630 |
| 5,211,165 A | 5/1993 | Dumoulin et al. | 128/653.1 |
| 5,368,487 A | 11/1994 | Medina | 434/262 |
| 5,403,191 A | 4/1995 | Tuason | 434/262 |
| 5,436,542 A * | 7/1995 | Petelin et al. | 318/567 |
| 5,589,838 A | 12/1996 | McEwan | 342/387 |
| 5,609,485 A | 3/1997 | Bergman et al. | 434/262 |
| 5,609,615 A | 3/1997 | Sanders et al. | 607/36 |
| 5,620,326 A | 4/1997 | Younker | 434/268 |

(Continued)

FOREIGN PATENT DOCUMENTS

DE   0 601 806   3/1993

(Continued)

OTHER PUBLICATIONS

"*Technical Advances in Hall-Effect Sensing*". (Product Description) Allegro® MicroSystems, Inc. Gilbert, Joe. 6 pages.

(Continued)

*Primary Examiner* — Xuan Thai
*Assistant Examiner* — Banafsheh Hadizonooz
(74) *Attorney, Agent, or Firm* — Ronald M. Anderson

(57) ABSTRACT

A videoendoscopic surgery training system includes a housing defining a practice volume in which a simulated anatomical structure is disposed. Surgical instruments can be inserted into the practice volume to access the anatomical structure. A digital video camera is disposed within the housing to image the anatomical structure on a display. The position of the digital video camera is supported within the practice volume by a camera bracket that enables a position of the video camera relative to the bracket to be selectively changed, thereby changing a viewing angle achieved by the video camera. In one embodiment the camera bracket is coupled to a boom, a proximal end of which extends outside the housing to enable additional positioning of the digital video camera by user adjustment of the proximal end of the boom. The housing preferably includes a light source configured to illuminate the anatomical structure.

21 Claims, 12 Drawing Sheets

U.S. PATENT DOCUMENTS

| | | | |
|---|---|---|---|
| 5,722,836 A | 3/1998 | Younker | 434/272 |
| 5,734,418 A | 3/1998 | Danna | 348/76 |
| 5,751,355 A * | 5/1998 | Bito et al. | 348/375 |
| 5,754,313 A | 5/1998 | Pelchy et al. | 358/473 |
| 5,800,178 A | 9/1998 | Gillio | 434/262 |
| 5,800,179 A | 9/1998 | Bailey | 434/262 |
| 5,832,772 A | 11/1998 | McEwan | 73/290 |
| 5,853,292 A | 12/1998 | Eggert et al. | 434/262 |
| 5,873,732 A | 2/1999 | Hasson | 434/262 |
| 5,883,591 A | 3/1999 | McEwan | 342/22 |
| 5,947,743 A | 9/1999 | Hasson | 434/262 |
| 6,074,213 A | 6/2000 | Hon | 434/262 |
| 6,095,148 A | 8/2000 | Shastri et al. | 128/898 |
| 6,113,395 A | 9/2000 | Hon | 434/262 |
| 6,139,489 A | 10/2000 | Wampler et al. | 600/109 |
| 6,211,904 B1 | 4/2001 | Adair et al. | 348/76 |
| 6,256,012 B1 | 7/2001 | Devolpi | 345/161 |
| 6,270,491 B1 | 8/2001 | Toth et al. | 606/11 |
| 6,428,323 B1 | 8/2002 | Pugh | 434/274 |
| 6,436,035 B1 | 8/2002 | Toth et al. | 600/249 |
| 6,470,302 B1 | 10/2002 | Cunningham et al. | 703/7 |
| 6,485,308 B1 | 11/2002 | Goldstein | 434/267 |
| 6,527,704 B1 | 3/2003 | Chang et al. | 600/112 |
| 6,532,379 B2 | 3/2003 | Stratbucker | 600/382 |
| 6,654,000 B2 | 11/2003 | Rosenberg | 345/156 |
| 6,659,776 B1 | 12/2003 | Aumann et al. | 434/262 |
| 7,114,954 B2 | 10/2006 | Eggert et al. | 434/273 |
| 2001/0000187 A1 | 4/2001 | Peckham et al. | 607/48 |
| 2002/0126501 A1 | 9/2002 | Toth et al. | 362/552 |
| 2003/0068607 A1 | 4/2003 | Gregorio et al. | 434/262 |
| 2003/0073060 A1 | 4/2003 | Eggert et al. | 434/262 |
| 2004/0033476 A1 | 2/2004 | Shun | 434/262 |
| 2004/0057718 A1* | 3/2004 | Chapman | 396/428 |
| 2004/0115607 A1 | 6/2004 | Pastrick et al. | 434/262 |
| 2004/0223078 A1* | 11/2004 | Zadok | 348/375 |
| 2005/0084833 A1* | 4/2005 | Lacey et al. | 434/262 |
| 2007/0178429 A1 | 8/2007 | Bell | 434/263 |

FOREIGN PATENT DOCUMENTS

| | | |
|---|---|---|
| DE | 4 212 908 | 10/1993 |
| EP | 0 624 861 | 5/1994 |
| FR | 0 217 689 | 11/1986 |
| FR | 2 691 826 | 12/1993 |
| GB | 2 338 582 | 12/1999 |
| WO | WO 93/21619 | 10/1993 |
| WO | WO 95/02233 | 1/1995 |
| WO | WO 2005/083653 | 9/2005 |

OTHER PUBLICATIONS

"*A Low-Power Hall-Effect Switch.*" Sensors Magazine, Jun. 1999. Christine Graham, 2 pages Allegro MicroSystems, Inc., USA <http://www.allegromicro.com/techpub2/3210/3210papr.htm>.

"*Differential Impedance Transducers*" Kaman Measuring Systems, 2004, 2 pages. <http://www.kamansensors.com/html/technology/technology-differential.htm>.

"*The Good, The Bad, and The Ugly*" Target material. Kaman Measuring Systems, 2004, 3 pages. <http://www.kamansensors.com/html/technology/technology-tntargetmaterial.htm>.

"*Variable Impedance Transducers*". Kaman Measuring Systems, 2004, 2 pages. <http://www.kamansensors.com/html/technology/technology-variable.htm>.

"*PNI SEN-S65 Magneto-Inductive Sensor.*" Mar. 2004, PNI Corporation, 5464 Skylane blvd., Santa Rosa, CA 95403-1084 USA. 1page. <http://www.pnicorp.com>.

"*Giant Magnetic Resistive Potentiometers with Strong Potentialities.*" (CORDIS focus, No. 45, Oct. 2003). 2pages. <http://www.sensorsportal.com/HTML/Potentiometers_Projects.htm>.

"*Non-contact Thread Detection.*" (Sensor Applications, Application Story, Mar. 2002). 2 pages. <http://www.sensorland.com/AppPage049.html>.

"*The Hall Effect.*" How they Work, How Sensors Work—HART Protocol. Sep. 22, 2004. 2 pages. <http://www.sensorland.com/HowPage046.html>.

* cited by examiner

LAPAROSCOPIC AND ENDOSCOPIC TRAINER INCLUDING A DIGITAL CAMERA WITH MULTIPLE CAMERA ANGLES

RELATED APPLICATIONS

This application is based on a prior copending provisional application Ser. No. 60/671,834, filed on Apr. 14, 2005, the benefit of the filing date of which is hereby claimed under 35 U.S.C. §119(e). This application is also a continuation-in-part of a copending patent application Ser. No. 10/672,274, filed on Sep. 24, 2003, the benefit of the filing date of which is hereby claimed under 35 U.S.C. §120.

BACKGROUND

In recent years many fully invasive surgical and operative medical procedures have been adapted to utilize videoendoscopic techniques to achieve minimally invasive procedures. Rather than requiring a relatively large incision to gain access to internal anatomical structures, videoendoscopic techniques require a plurality of much smaller incisions. Generally, one incision is made for a videoendoscopic camera, and two or more incisions are made to introduce surgical instruments. The diameters of the surgical instruments and the probe for the videoendoscopic camera are made as small as practical, to minimize the size of the incisions that are required. The endoscope is used to enable the surgeon to view, in real-time, the surgical field and the manipulation of the endoscopic instruments within that field.

The majority of the videoendoscopic cameras in use today employ an optical fiber to transmit an image of the internal surgical field to a video camera that is disposed externally. Exemplary videoendoscopic cameras are described in U.S. Pat. No. 6,527,704 (Chang et al.). As indicated in FIGS. 1A and 1B of the Chang et al. patent, such systems tend to include a plurality of external components that are mounted together in a rack that can be moved from one operating theater or room to another, as required. While such systems work well in a surgical theater, their size, weight, limited mobility, and cost make such systems ill-suited for use in a training environment, where highly portable and lower cost devices are very desirable.

As technology improves so as to enable a substantial reduction in the size of video cameras, it has been suggested to employ small internal video cameras that have been inserted within the body of a patient, instead of using an optical fiber to transmit the image from the surgical field to an external video camera. Systems of this type are described in U.S. Pat. No. 5,754,313 (Pelchy et al.), U.S. Pat. No. 6,139,489 (Wampler et al.), and U.S. Pat. No. 6,211,904 (Adair et al.). However, at the present time, small video cameras that can be disposed at an internal surgical field have not supplanted more conventional videoendoscopic systems that employ fiber optics to transmit internal images to an external camera, either for actual surgical use or in a training context, such as simulations or skill development exercises.

The need for endoscopic surgical training systems is significant. Hand eye coordination skills useful in conventional surgery do not translate well into endoscopic surgery. In conventional surgery, a surgeon is able to look directly at the treatment site, and is generally able to see his hands and the instruments in the surgical field in three dimensions. In videoendoscopic surgery, the surgeon is not able to feel the tissue and/or organs associated with an operative site first hand, because the surgeon remotely manipulates the tissue and/or organs using elongate surgical tools from outside the surgical field. Further, the surgeon observes a two-dimensional image of the surgical field. The ability to work from a two-dimensional image of the surgical field, while remotely manipulating instruments, requires a significant amount of training. It is critical that surgeons be taught and thereafter practice videoendoscopic skills that will help them to identify structures and carefully control endoscopic instruments, to ensure that surgical procedures are accurately performed, and to avoid unnecessary damage to surrounding tissue. Even basic surgical skills, such as suturing and knot tying, become challenging when performed endoscopically. In a videoendoscopic environment, such basic surgical tasks require great skill and precision, which can only be achieved through training and practice.

For surgeons or students who require basic training, skills unique to videoendoscopic surgery need to be learned. Two-dimensional recognition skills must be learned, as well as the manipulation of objects using elongate surgical instruments. Another skill that needs to be learned is the ability to use such elongate surgical instruments to manipulate objects when the view of the workspace is very restricted.

A wide variety of different elongate surgical instruments have been developed, and continue to be developed, for use in endoscopic surgery. Even surgeons who have mastered two-dimensional recognition skills and the manipulation of objects using elongate surgical instruments welcome the opportunity to familiarize themselves with new instruments in a training context, prior to using such instruments during an actual procedure.

Surgeons and other medical personnel can be trained in endoscopic surgical techniques using animal specimens or human cadavers. However, such training methods are very expensive, since animals and cadavers are in limited supply and cannot be used repeatedly. Also, animal specimens and human cadavers are not readily portable.

Many endoscopic techniques, such as instrument manipulation, can be successfully learned using simple box trainers. Such trainers generally include a housing in which a simulated anatomical structure is placed. Students can manipulate instruments passing through openings in the housing to gain confidence in such skills as suturing and knot tying. Some box trainers have openings through which the student can look to directly observe the simulated anatomical structure. While such a trainer is effective for gaining skills related to remote manipulation of endoscopic instruments, since the trainee looks directly at the simulated anatomical structure, two-dimensional recognition skills cannot be learned and practiced. Thus, some box trainers employ mirrors that reflect an image of the practice site, so that the trainee can also gain the necessary two-dimensional recognition skills. U.S. Pat. No. 5,722,836 (Younker) discloses one such box trainer.

Box trainers are relatively inexpensive and very portable, and are therefore desirable teaching tools. It must be recognized, however, that box trainers, including those that employ mirrors to develop two-dimensional recognition skills, do not provide a very realistic simulation of a true videoendoscopic procedure. During an actual endoscopic procedure, the surgeon will be observing an image displayed on a monitor. While a conventional endoscopic camera could be introduced into a box trainer to provide a video image of the simulated anatomical structure at a practice site, conventional endoscopic cameras are not very portable, and are very expensive. Such a training system, while being more realistic in simulating an actual surgical environment than a box trainer with a mirror, no longer offers the low cost and portability of a box trainer alone. It would thus be desirable to provide a low cost and highly portable trainer that is capable of providing a video image of a practice volume and of remotely manipulated endoscopic instruments being utilized within the practice volume.

SUMMARY

The concepts disclosed herein encompass a surgical trainer for practicing videoendoscopic surgical techniques. The surgical trainer includes a relatively low-cost, portable digital camera disposed within the trainer, configured to provide a substantially real-time image of a practice volume defined by the trainer housing. Various embodiments are contemplated, including embodiments in which the digital camera is selectively positionable to obtain an image of different portions of the practice volume.

An exemplary embodiment of the surgical trainer includes a camera mounting bracket for coupling a digital camera to an elongate member. The camera mounting bracket includes a plurality of different positions for mounting the digital camera, which enables the same trainer to simulate endoscopes and laparoscopes providing a variety of different viewing angles. Often a lens or light collecting element at the distal end of endoscope or laparoscope is disposed at a normal angle relative to the generally elongate body of the endoscope (this configuration achieves what is referred to as a 0° viewing angle). However, endoscopes and laparoscopes are available that provide a different viewing angle, by placing the lens or light collecting element at a different angle relative to the generally elongate body of the endoscope. FIG. 10A schematically illustrates the distal portions of four different prior art endoscopes exhibiting optical viewing angles of 0°, 20°, 30°, and 45°. These optical angles can be readily achieved when the light collecting element is an optical fiber, simply by cutting the distal end of the optical fiber at the desired angle. With respect to the concepts disclosed herein, duplicating the different viewing angles with which clinicians are familiar is more problematical, because a digital camera is used in place of the optical fibers employed in conventional endoscopes and laparoscopes. This problem can be solved according to the concepts disclosed herein with the use of a camera mounting bracket enabling a plurality of different viewing angles to be achieved.

Before describing the camera mounting bracket, an exemplary surgical trainer including a digital camera will be described. This exemplary surgical trainer includes a housing defining a practice volume, and a digital camera disposed within the practice volume. The digital camera is configured to capture a plurality of frames per second, such that the digital camera can provide a video feed imaging of at least a portion of the practice volume. Preferably, an anatomical structure is disposed in the practice volume. In at least one embodiment, the anatomical structure is disposed within a lower portion of practice volume. The digital camera is positioned within the practice volume relative to the anatomical structure such that a video feed signal imaging the anatomical structure obtained using the digital camera realistically simulates a video feed of an internal surgical field obtained by either a conventional laparoscopic camera or a conventional endoscopic camera.

The housing is preferably configured to enable a trainee to insert elongate medical tools (i.e., endoscopic tools) into the practice volume to perform either a simulated procedure upon the anatomical structure by manipulating the elongate medical tools from outside the housing, or to perform endoscopic skills training exercises. The position of the digital camera within the housing is selected to ensure that the digital camera does not interfere with a range of motion required by the elongate medical tools to successfully perform the simulated procedure or exercises.

In some embodiments, the digital camera is movably positionable within the practice volume so that when a position of the anatomical structure is changed, the position of the digital camera can be changed to continue to provide a video feed imaging the anatomical structure, although it should be recognized that the camera mounting brackets described herein can also be implemented in surgical trainers where the digital camera is not configured to be movably positionable by a user during a training exercise. Embodiments wherein the digital camera is configured to be fixed in a position within the housing are particularly well-suited for training beginning students, since the emphasis of the training is on gaining expertise with the manipulation of endoscopic tools while viewing the distal end of the tools on a monitor, without allowing the student to directly observe the tools and work area. More experienced students will benefit from embodiments that also enable the student to manipulate the position of the digital camera within the workspace (i.e., within the housing) while practicing a medical procedure. Movement of the digital camera enables a field of view obtained by the digital camera to be varied. Such movement enables the digital camera to obtain an image of at least a portion of the practice volume from a plurality of different angles. Preferably, movement of the digital camera will enable the proximity of the digital camera to be varied relative to at least a portion of the practice volume. Movable and positionable digital cameras are particularly beneficial for training involving the simulation of an actual endoscopic procedure, such as suturing, because endoscopic procedures often require the field of view provided by the endoscope, which is generally quite limited, to be shifted as the procedure progresses. As discussed in more detail below, it is particularly advantageous if the digital camera can be moved in a manner that enables the digital camera to move closer to (or farther from) a desired portion of the practice volume (i.e., to zoom in on, or away from a particular portion of the practice volume). This ability simulates a technique often employed in videoendoscopy, i.e., moving a laparoscope or endoscope closer to (or away from) a particular portion of a surgical field, to zoom in (or out, respectively) relative to a specific portion of the surgical field. In another embodiment, the position of the digital camera is fixed, and the digital camera is configured to image a predefined portion of the practice volume. Trainers having digital cameras in fixed positions are particularly useful for skill based training exercises, such as basic instrument manipulation and two-dimensional recognition skills. If the field of view provided by a fixed digital camera is sufficiently broad, or if the simulated anatomical structure or other work piece can readily be repositioned relative to the digital camera, such an embodiment can also be used for simulating an actual endoscopic procedure.

To achieve an embodiment enabling a student to selectively change the position of the digital camera, an exemplary configuration includes an elongate member having a proximal end disposed outside the practice volume, and a distal end disposed inside the practice volume. The digital camera is coupled with the distal end of the elongate member, such that a manipulation of the proximal end of the support structure changes a position of the digital camera within the practice volume. In at least one embodiment, the proximal end of the elongate member includes a handle configured to simulate the handle of a conventional laparoscope. Embodiments that include an elongate member structure preferably also include a mounting bracket configured to support the elongate member. In some embodiments, the mounting bracket is configured to slidingly engage the elongate member, such that an amount of the elongate member disposed within the practice volume can be increased or decreased as desired. Such movement enables the digital camera to move closer to, or away from portions of the practice volume, enabling the digital camera to zoom in or out relative to a work surface being imaged thereby. While some digital cameras include digital and/or optical zoom adjustments, requiring or enabling a user to manipulate the elongate member to achieve a desired zoom simulates the manipulation required of a conventional laparoscope or endoscope to achieve a similar zoom, increasing a realism of the training experience. In some embodiments, the mounting bracket is configured to pivotally engage the elongate member, such that a position of the distal end of the elongate member within the practice volume can be adjusted. In some embodiments, the mounting bracket is configured to pivotally engage the housing, such that a position of the distal end of the elongate member within the practice volume can be adjusted. Particularly preferred mounting brackets enable different ranges of motion to be achieved.

Generally, a size of the digital camera is significantly larger than a size of a distal end of a conventional laparoscope, such that the digital camera could not pass through an incision configured to receive a conventional laparoscope. The use of a larger digital camera enables relatively inexpensive digital cameras, such as web cams, to be employed in this application.

The camera mounting bracket enabling a plurality of different viewing angles to be achieved is configured to selectively positionally couple the digital video camera (i.e., the digital camera) to a support structure used to secure the digital camera to the surgical trainer. As noted above, in an exemplary embodiment enabling a user to selectively move the digital camera within the training volume, the support structure can be an elongate member. In other exemplary embodiments, the support structure simply secures the digital camera within the interior of the housing. In still other exemplary embodiments, the camera mounting bracket is attached directly to the housing.

The camera mounting bracket is configured to enable the position of the digital camera relative to the support structure (or housing) to be selectively modified. In an exemplary but not limiting embodiment, the camera mounting bracket enables at least two of the following optical viewing angles to be achieved: 0°, 20°, 30°, and 45°. The camera mounting bracket may be formed from a variety of different materials, such as metal or plastic. In an exemplary embodiment, the size and shape of the mounting bracket are such that injection molding techniques can be readily used to produce the mounting brackets in quantity.

In an exemplary embodiment, the camera mounting bracket is secured to the digital camera via a threaded shaft that engages a threaded opening formed into the digital camera. A proximal end of the threaded shaft is coupled to an adjustment knob. In one exemplary embodiment, the camera mounting bracket includes three different openings, each corresponding to one of three different mounting positions. The threaded shaft can be placed into the opening selected, and then into the threaded opening in the digital camera. The knob can be used to screw the threaded shaft into the threaded opening, thereby securing the digital camera to the camera mounting bracket. In such an exemplary embodiment, one mounting position corresponds to a 0° viewing angle, a second mounting position corresponds to a 30° viewing angle; and the final opening corresponds to a 45° viewing angle. Those of ordinary skill in the art will readily recognize that additional viewing angles can be achieved by forming additional and/or differently disposed openings in other portions of the camera mounting bracket. Furthermore, it should be recognized that while the above described exemplary embodiment includes three openings enabling three different mounting positions to be achieved, it should be understand that the specific number of different mounting positions achievable using such a camera mounting bracket can be varied, and that three different mounting positions (achieving three different viewing angles) is simply exemplary, and is not intended to limit the concepts disclosed herein.

Yet another exemplary embodiment of a mounting bracket includes only a single opening, forming a generally elongate channel in the camera mounting bracket. Once again a threaded shaft (having a knob on its proximal end) is introduced into the single opening and used to secure the digital camera to the camera mounting bracket (threads on the distal end of the shaft engaging threads in an opening on the digital camera). Such a camera mounting bracket is not limited to only three viewing angles, but is infinitely positionable between a minimum viewing angle (preferably corresponding to about 0°, although such a preference is intended to be exemplary, rather than limiting) and a maximum viewing angle (preferably corresponding to about 45°, although again, such a preference is intended to be exemplary, rather than limiting). Markings can be formed into or applied on the camera mounting bracket to indicate the position of frequently used viewing angles, such as 45° or 30°. A graduated scale can be included with the camera mounting bracket so that the clinician can determine what viewing angle is associated with the particular portion of the opening.

With respect to the use of threaded shaft and knob being used to securely attach a digital camera to the camera mounting bracket, it should be understood that such an attachment mechanism is merely exemplary, and not intended to limit the concepts disclosed herein. Those of ordinary skill in the art will readily recognize that many other different mechanical configurations can be used to attach an item such as a digital camera to a camera mounting bracket.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 schematically illustrates a Prior Art box trainer for use in teaching endoscopic surgical skills to surgeons and students;

FIG. 2 schematically illustrates a system for teaching endoscopic surgical skills to surgeons and students in accord with the novel concepts disclosed herein;

Figure 7A:
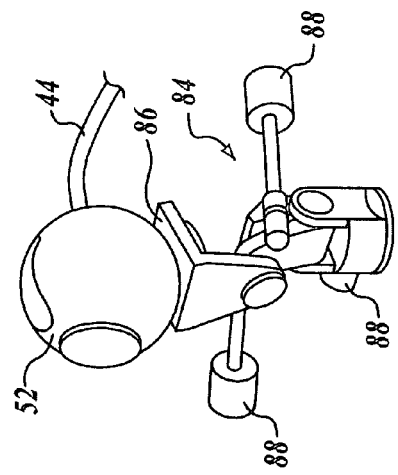
Figure 7B:
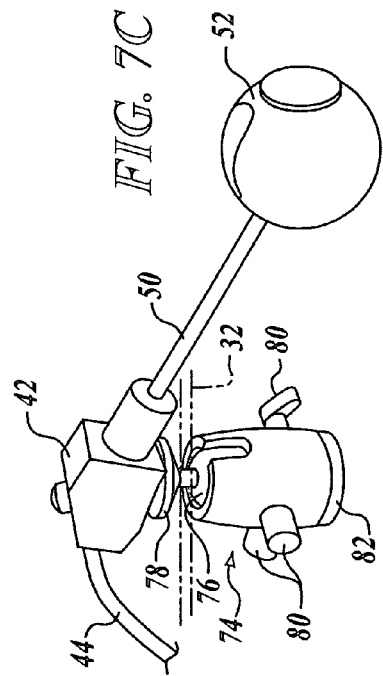
Figure 7C:
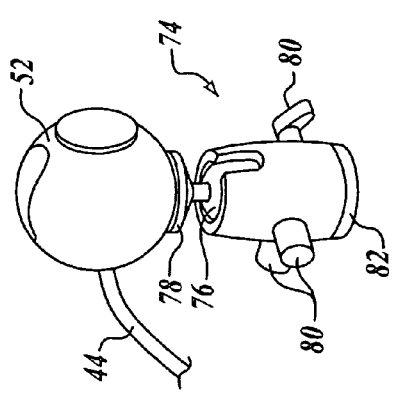
Figure 8:
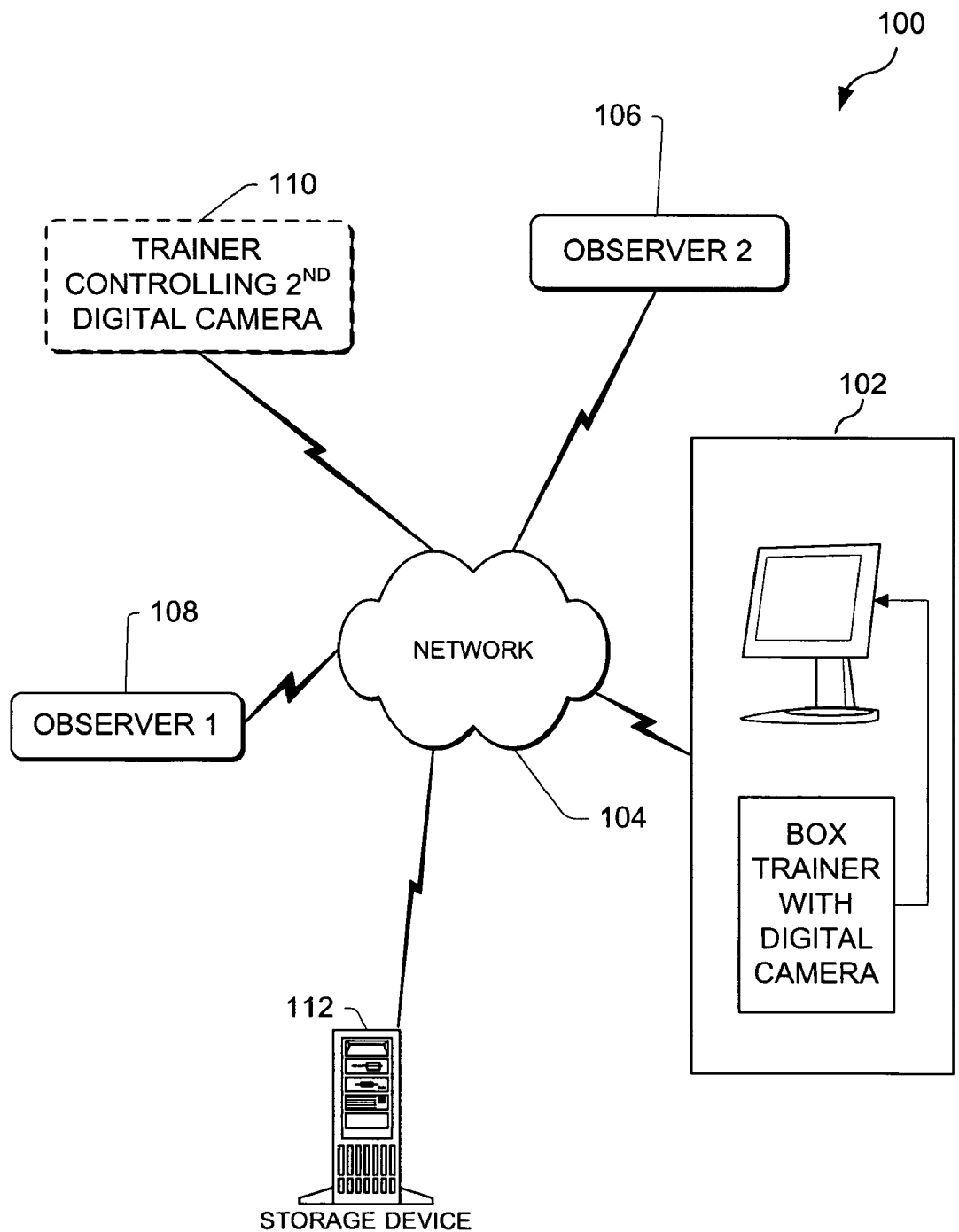
Figure 9A:
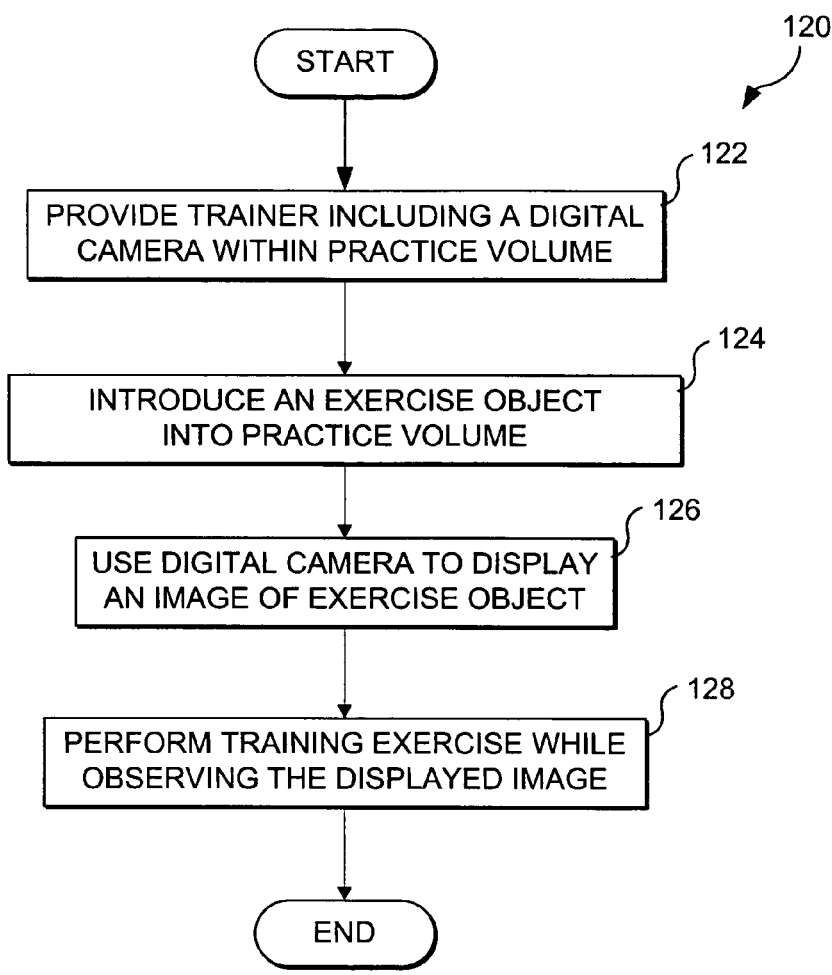
Figure 9B:
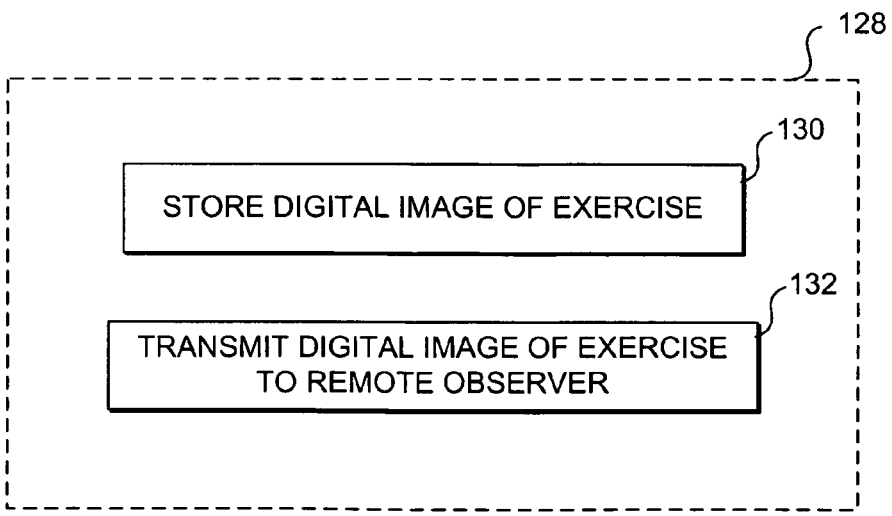
Figure 10A:
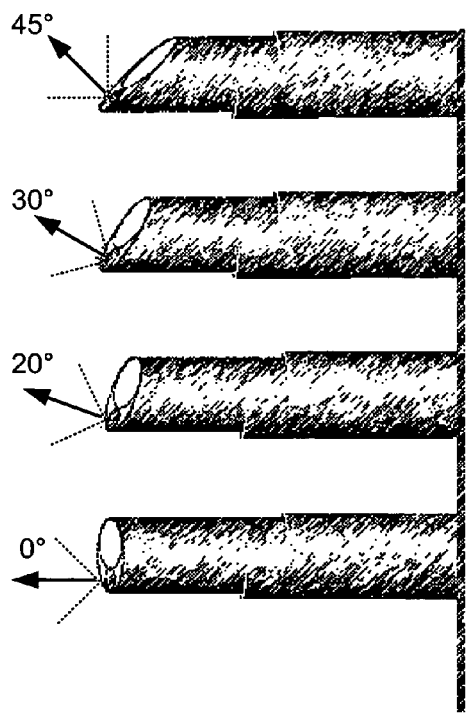
Figure 10B:
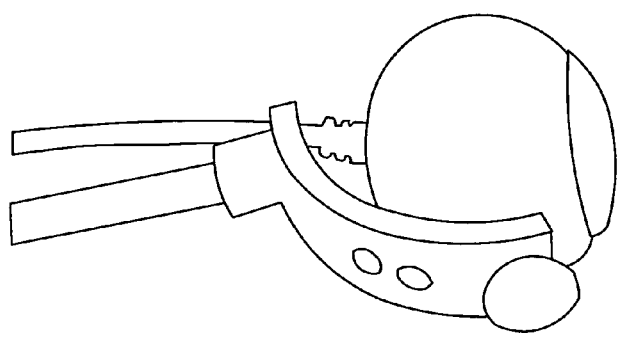
Figure 10C:
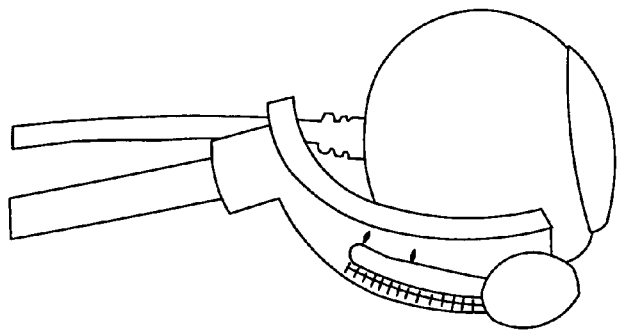
Figure 11A:
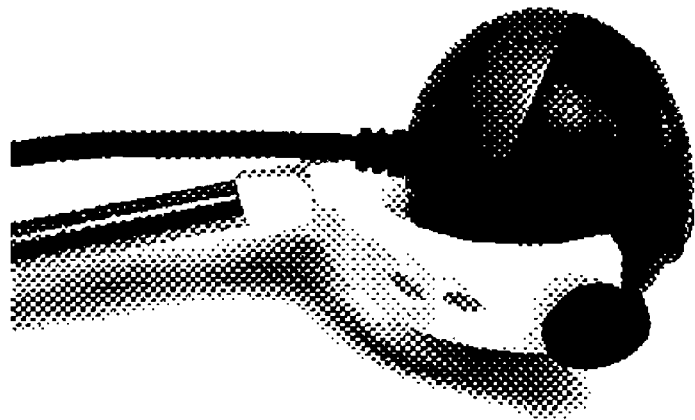
Figure 11B:
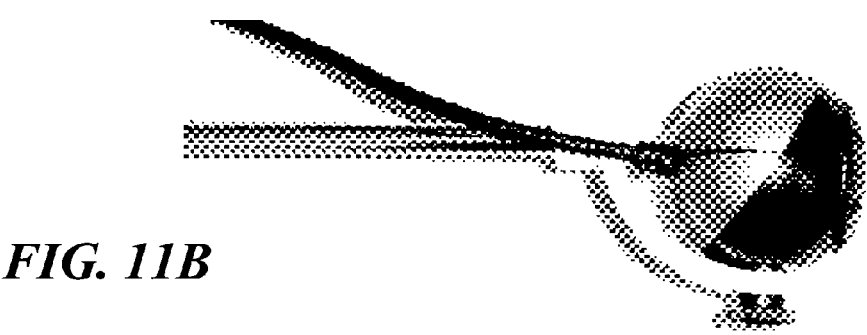
Figure 11C:
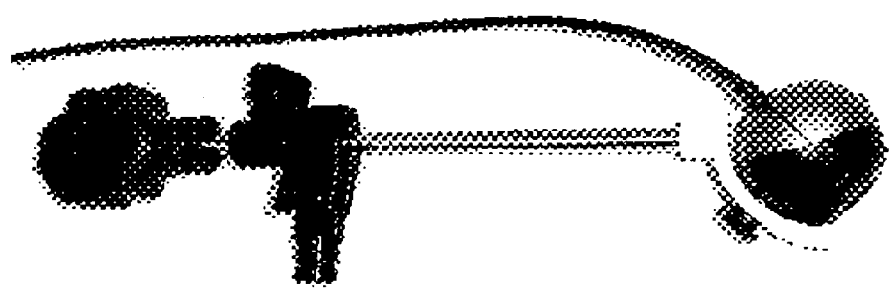
Figure 11D:
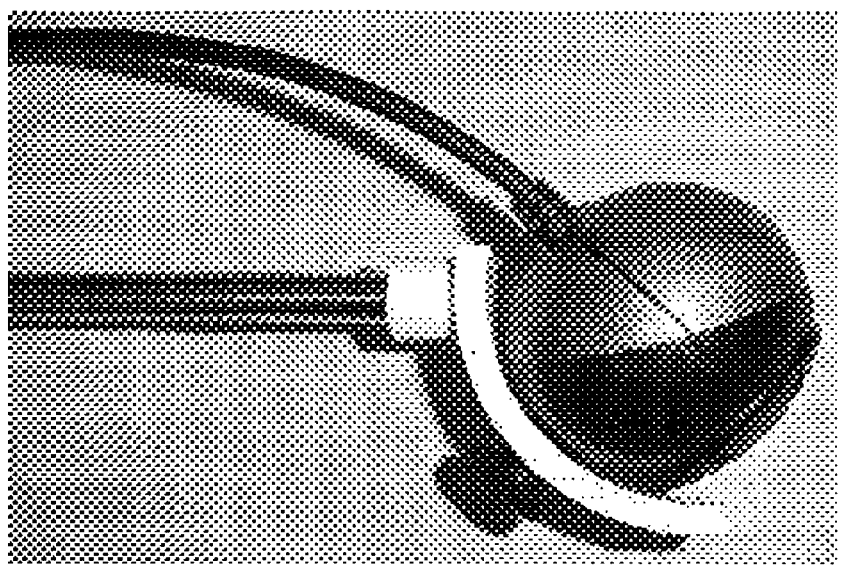
Figure 11E:
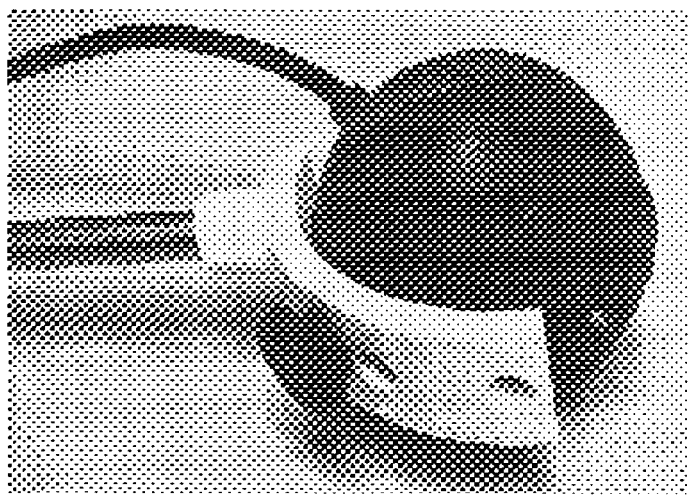

FIG. 7A schematically illustrates a digital camera coupled with a ball mount, such that when the digital camera and ball mount are disposed inside the trainer, the digital camera can be selectively positioned to focus on a particular portion of the practice volume defined by the housing;

FIG. 7B schematically illustrates a digital camera coupled with a pan and tilt head, such that when the digital camera and the pan and tilt head are disposed inside the trainer, the digital camera can be selectively positioned to focus on a particular portion of the practice volume defined by the housing;

FIG. 7C schematically illustrates an elongate member whose proximal end is coupled with a ball mount, and whose distal end is coupled with a digital camera, such that when the ball mount is disposed outside a housing and the digital camera is disposed within the housing, manipulation of the ball mount selectively repositions the digital camera, enabling the digital camera to be directed to capture an image of a particular portion of the practice volume defined by the housing;

FIG. 8 schematically illustrates an exemplary configuration in which a training system in accord with the concepts disclosed herein is coupled to a network, so that images of a training exercise obtained using the digital camera disposed within the practice volume of the training system are transmitted to remote observers who are also coupled to the network;

FIG. 9A is a logical flow diagram showing steps in accord with a method for enhancing videoendoscopic skills training using a digital video camera disposed within the practice volume of a trainer;

FIG. 9B schematically illustrates optional logical steps associated with the logical flow diagram of FIG. 9A;

FIG. 10A schematically illustrates a plurality of different prior art endoscopes, each endoscope having a different distal configuration enabling a different viewing angle to be achieved;

FIG. 10B schematically illustrates a multi-position camera bracket coupling a digital camera to an elongate member, such that the digital camera is attached to the multi-position camera bracket using a first one of three different possible attachment positions, the bracket enabling three different viewing angles to be achieved;

FIG. 10C schematically illustrates a multi-position camera bracket coupling a digital camera to an elongate member, such that the digital camera is attached to the multi-position camera bracket using a first one of a plurality of different possible attachment positions, the bracket enabling an infinite number of viewing angles to be achieved between a minimum viewing angle and a maximum viewing angle;

FIGS. 11A and 11B are monochromatic images of a multi-position camera bracket coupling a digital camera to an elongate member, such that the digital camera is attached to the multi-position camera bracket using a first one of three different possible attachment positions;

FIGS. 11C and 11D are monochromatic images of a multi-position camera bracket coupling a digital camera to an elongate member, such that the digital camera is attached to the multi-position camera bracket using a second one of three different possible attachment positions; and FIG. 11E is a monochromatic image of a multi-position camera bracket coupling a digital camera to an elongate member, such that the digital camera is attached to the multi-position camera bracket using a third one of three different possible attachment positions.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive.

Figure 1:
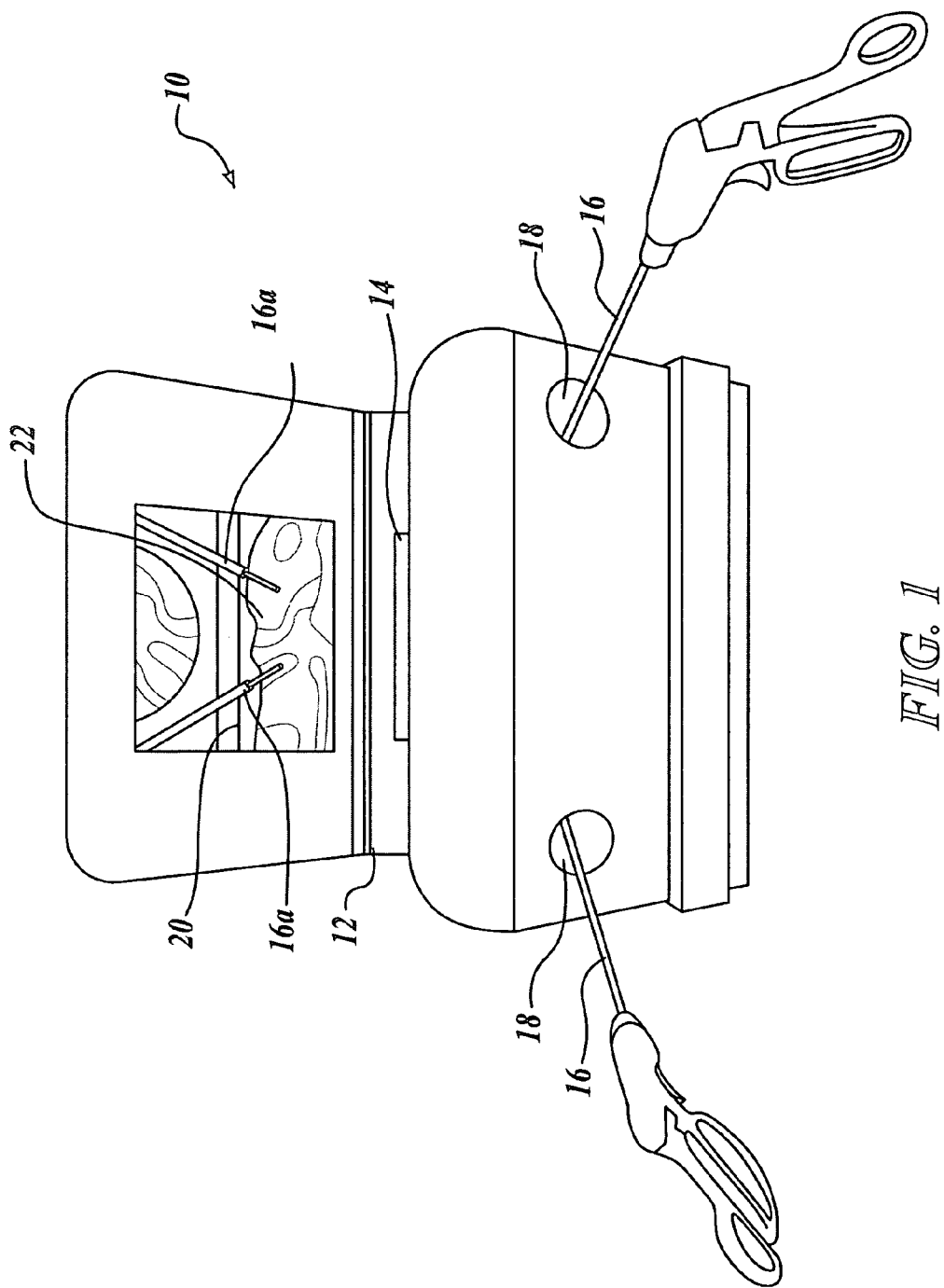

FIG. 1 schematically illustrates a prior art surgical trainer 10 that is configured for video endoscopic surgery training. Trainer 10 includes a housing 12. An anatomical structure 14 is disposed within housing 12, such that portions of housing 12 prevent a trainee from clearly viewing anatomical structure 14. Housing 12 includes a plurality of openings 18 into which surgical instrument 16 can be inserted. Preferably, surgical instruments 16 are endoscopic suturing instruments such as an ENDO STITCH endoscopic reciprocating suturing instrument manufactured by U.S. Surgical, Inc. Trainer 10 includes a reflector 20 in which an image 22 of anatomical structure 14 can be observed by a trainee. Note that distal ends 16a of surgical instruments 16 can be seen within image 22. Surgical trainer 10 thus provides a trainee with an opportunity to practice endoscopical surgical techniques such as suturing and knot tying, as well as gaining experience in two-dimensional pattern recognition. However, image 22 does not realistically simulate an image displayed on a video monitor, such as a surgeon would view during an actual endoscopic procedure.

Figure 2:
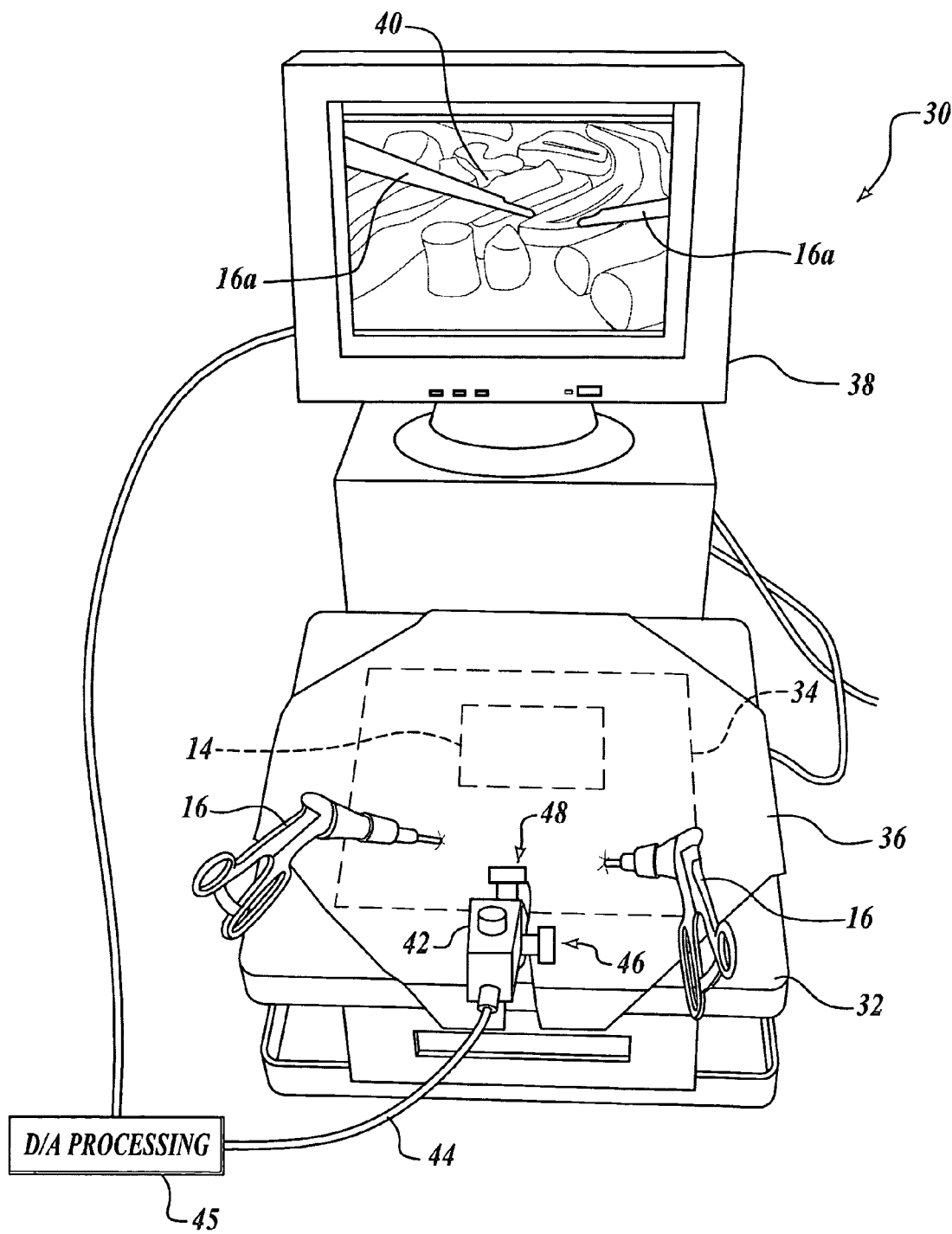

FIG. 2 schematically illustrates a training system 30 in accord with the concepts disclosed herein, which provides the same type of image a surgeon would view during an actual endoscopic procedure. System 30 includes a box trainer into which a digital camera is disposed within a practice volume defined by the box trainer. The digital camera is connected to a computing device (not separately shown), which drives a display 38, so that a trainee can observe a simulated surgical field upon the display, generally as would be experienced during an actual endoscopic or laparoscopic procedure. The trainer portion of system 30 is preferably implemented using a box trainer having a housing 32 that defines the practice volume within the housing. An upper portion of housing 32 includes an opening 34, which is covered by either a clear or an opaque cover 36. An opaque cover prevents a trainee from viewing the practice area and encourages the trainee to view the progress of a simulated endoscopic procedure on display 38.

A simulated anatomical structure 14 is contained within housing 32. One or more surgical instruments 16 pass through openings in cover 36 to access the practice volume defined by housing 32. In one embodiment, cover 36 is a plastic sheet that is placed over opening 34. When a trainee desires to introduce instruments 16 into the practice volume, holes can readily be formed into cover 36 using a scalpel or other object to pierce the cover. Instruments 16 are then introduced into housing 32. Of course, if desired, a trocar stop (not shown) may be inserted into a flexible elastomeric cover that is placed over opening 34, and a trocar (not shown) may be inserted into each trocar stop, to more realistically simulate the preparation of a patient for a laparoscopic procedure. Surgical instruments 16 may then be inserted through the trocars for increased realism in the training provided.

Figure 3:
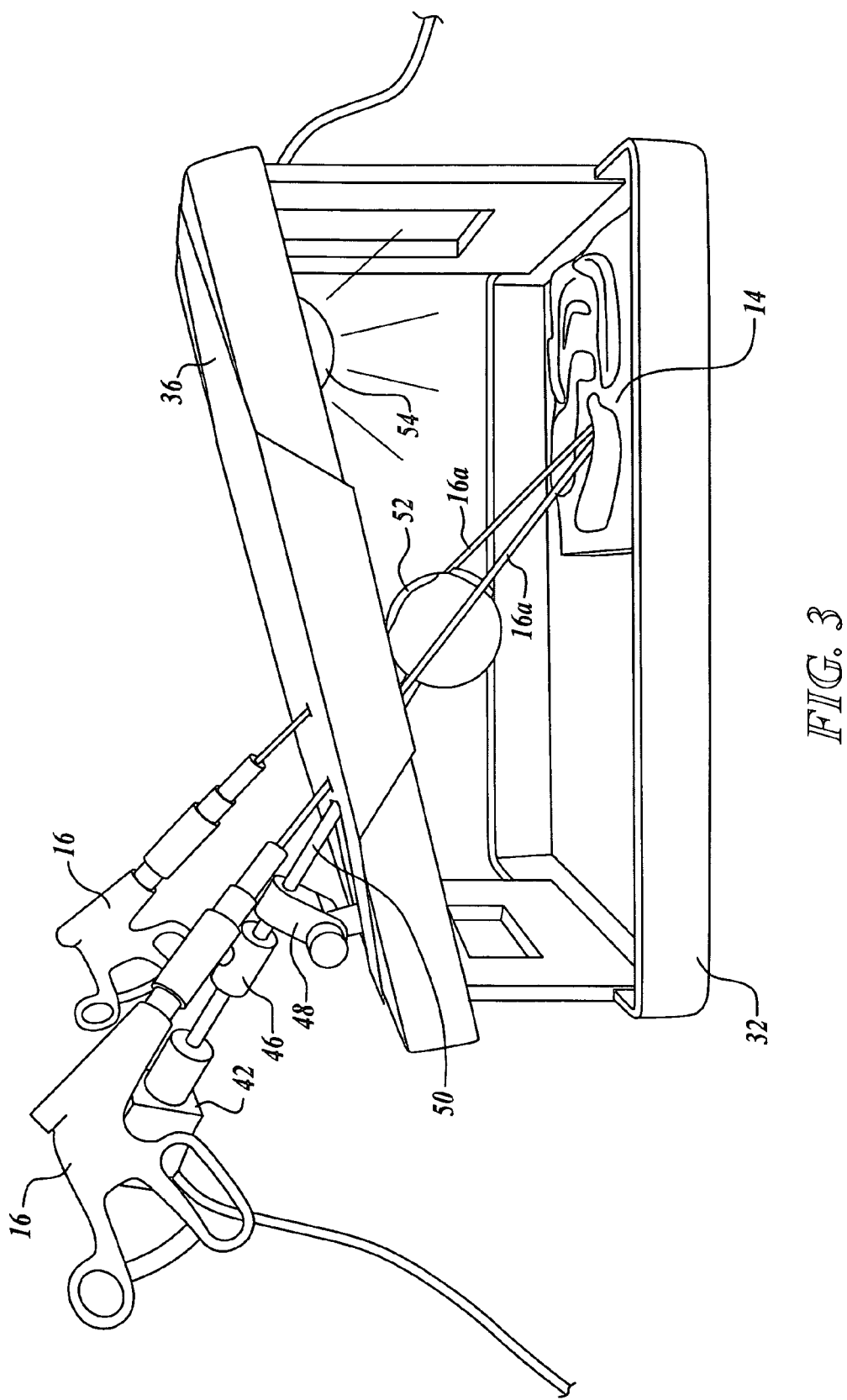
FIG. 3 is a side elevational view of a surgical trainer including a digital camera disposed inside the trainer according to a first embodiment that employs the concepts disclosed herein.

A digital camera is disposed within housing 32 and provides an output signal through output line 44 (the camera is obscured by cover 36 in FIG. 2, but can be clearly seen in FIG. 3). The output signal is used to provide a video signal for use in driving display 38. A simulated laparoscope handle 42 is included for positioning the camera to provide additional realism. As will become clear in the Figures discussed below, the digital camera is coupled with a distal end of an elongate member, and simulated laparoscope handle 42 is coupled to a proximal end of the elongate member. A trainee can then grasp the simulated laparoscope handle and move the digital camera throughout the practice volume defined by housing 32. Mounting brackets 48 and 46 movably support the elongate member.

The output signal provided by the digital camera generally requires processing to achieve a video signal suitable for driving the display. Many displays are configured to process only video red, green, blue (RGB) analog signals. Some more expensive digital cameras include digital-to-analog circuitry that produces an analog output signal suitable to drive an analog display, although it is preferred to employ a low cost digital camera (to reduce the cost of the system), which typically does not provide a video analog output signal that can directly drive an analog display. Desktop personal and laptop computers are ubiquitous, and can readily accomplish the necessary digital-to-analog signal processing required to achieve an analog signal that can be displayed on equally ubiquitous RGB analog video monitors. Further, desktop personal and laptop computers can be used to perform signal processing required so that the output signal produced by a digital camera is converted to a display signal that can be used to drive many different types of displays. Indeed, the use of a computing device such as a desktop personal computer or a laptop computer enables relatively low cost web cameras to be utilized as the digital camera. Those of ordinary skill in the art will recognize that an output signal from a digital camera can be processed to produce a display signal for many different types of display devices, including televisions configured to display an NTSC signal, televisions configured to display a PAL signal, cathode ray tube based computer monitors, LCD monitors, and plasma displays.

As shown in FIG. 2, output line 44 is coupled to a digital-to-analog converter 45, which is then connected to display 38, upon which an image 40 can be viewed. It should be understood that image 40 is obtained by a digital camera disposed within housing 32, and image 40 provides a view of distal ends 16a of surgical instruments 16 and a portion of simulated anatomical structure 14. It should be further understood that converter 45 can be implemented using a laptop or personal computer, or less desirably, by a converter circuit specifically provided for this purpose. Note that converter 45 is not required if display 38 is configured to utilize an output signal from the digital camera. It should be understood that converter 45 is configured to produce a display signal matched to the type of display 38 being employed.

It should be understood that system 30 does not require that simulated anatomical structure 14 be provided in order for the system to be used for videoendoscopic skills training. While the inclusion of simulated anatomical structure 14 does enable system 30 to be used to simulate an endoscopic or laparoscopic procedure such as suturing, system 30 can also be used for more basic videoendoscopic skills training without employing the simulated anatomical structure. For example, two-dimensional recognition skills and remote instrument manipulation are two skills that must be mastered before an endoscopic surgical procedure is simulated or attempted. For training emphasizing two-dimensional recognition skills and remote instrument manipulation, other types of objects can be substituted for simulated anatomical structure 14. Thus, a basic training exercise can be carried out using system 30 and a plurality of grains of rice that are placed within the practice volume defined by housing 32. While observing the progress of the training exercise on display 38, the trainee is instructed to use instruments 16 to move each grain of rice from one part of the practice volume to another. In such an exercise, the distal ends of instruments 16 will include forceps that the trainee manipulates remotely. While such a training exercise may seem trivial, execution of this exercise provides the trainee with practical experience in two-dimensional recognition, remote manipulation of instruments, working within a limited field of view provided by the digital camera (conventional laparoscopes and endoscopes provide a limited field of view), and performing a repetitive task under such conditions. Each such element directly relates to a skill required in endoscopic surgery. Of course, objects other than grains of rice can be similarly utilized.

The incorporation of an inexpensive digital camera within the practice volume of a box trainer achieves a very useful videoendoscopic surgical trainer. Because the digital camera is within the practice volume, the images obtained realistically simulate the type of images that are obtained using laparoscopes and endoscopes during actual surgical procedures. Regardless of whether the object in the practice volume that is being imaged is a simulated anatomical structure or some object being manipulated to develop instrument skills, having the digital camera within the practice volume, close to the object being manipulated, enables a narrow field of view to be achieved. Particularly when the digital camera is movable within the practice volume, trainees have an opportunity to selectively vary the field of view obtained by the camera, the angle of the camera relative to the objects, and the proximity of the camera to the object (i.e., the closer the camera, the larger the object will appear in the image). An important element of endoscopic surgery is properly positioning the endoscope (or laparoscope) to obtain a useable image of the surgical field.

FIG. 3 is side view of the trainer of system 30. A digital camera 52 can clearly be seen inside the practice volume defined by housing 32. Anatomical structure 14 is being manipulated by distal ends 16a of surgical instruments 16. As noted above, objects other than simulated anatomical structure 14 can be placed within the practice volume for endoscopic skills training. A light source 54 illuminates anatomical structure 14 so that digital camera 52 can obtain a clear image of anatomical structure 14 and distal ends of surgical tools 16. Digital camera 52 is coupled to a distal end of an elongate member 50, which passes through an opening formed in cover 36. Elongate member 50 is supported by a mounting bracket 48 and a mounting bracket 46. Simulated laparoscope handle 42 is attached to the proximal end of elongate member 50. Elongate member 50 is a hollow shaft, and output line 44 from digital camera 52 passes through the shaft to simulated laparoscope handle 42. The output line is then coupled to a computing device as described above, if conversion of the digital signal to produce an RGB analog signal is required.

Figure 4:
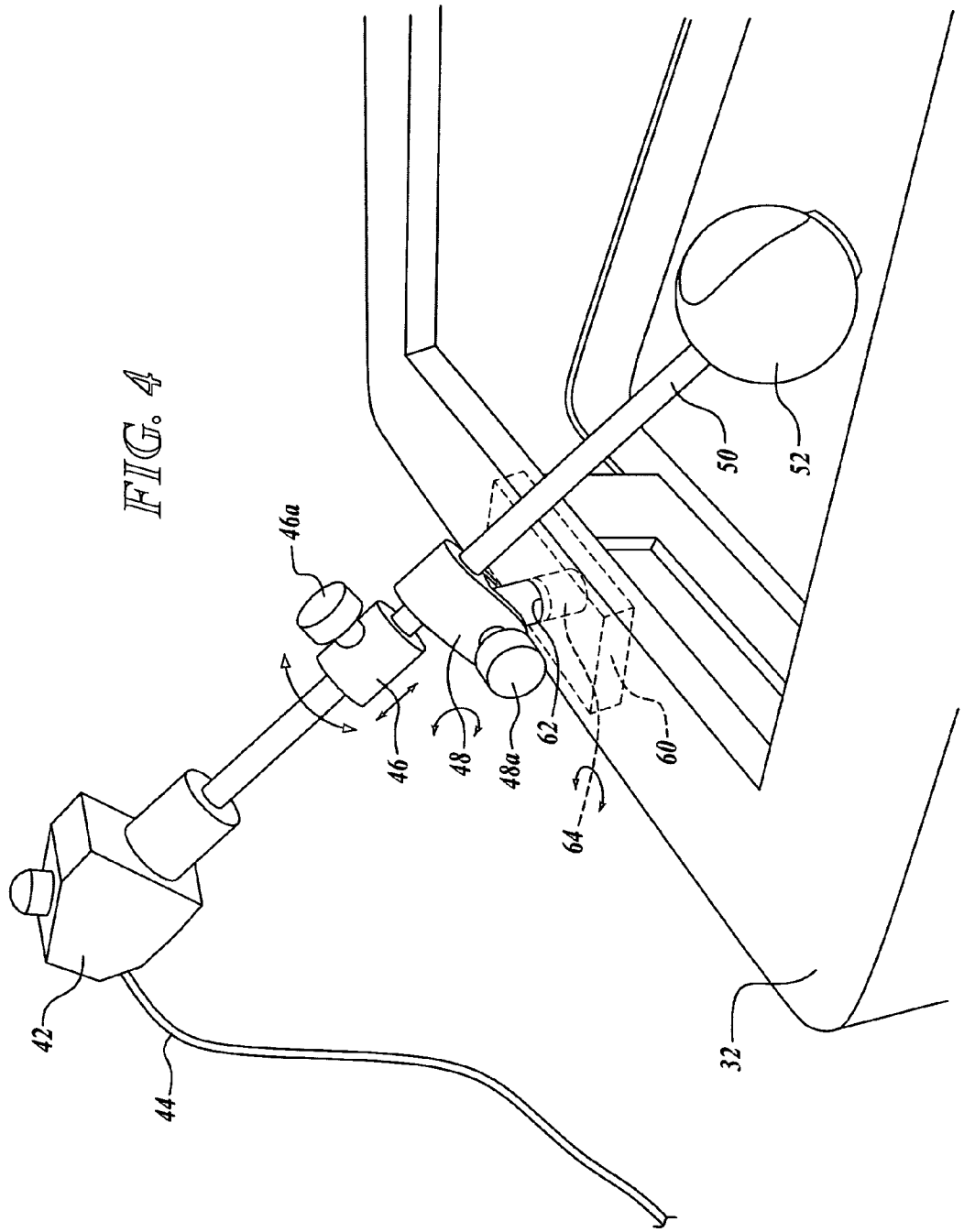
FIG. 4 is a partial view of the upper portion of the surgical trainer of FIG. 3, providing a detailed view of the exemplary support structure for the digital camera, illustrating how the support structure enables zooming, panning, and tilting of the digital camera to be achieved.

FIG. 4 provides additional details showing how mounting brackets 48 and 46 movably support elongate member 50. Cover 36 has been omitted from FIG. 4 to enable the relationship between digital camera 52, elongate member 50, and mounting brackets 48 and 46 to be more clearly shown. Mounting bracket 46 substantially encompasses elongate member 50 and includes an adjustment knob 46a. When adjustment knob 46a is loosened, the elongate member 50 can be freely moved relative to mounting brackets 46 so that a trainee can adjust the position of elongate member 50 within the practice volume, relative to housing 32. Because digital camera 52 is fixedly coupled with elongate member 50, introducing more of elongate member 50 into the practice volume moves the digital camera closer to a lower portion of the practice volume. This movement of the digital camera is indicated by the arrow disposed adjacent to mounting bracket 46. Note that when adjustment knob 46a is loosened, elongate member 50 can also be rotated, causing digital camera 52 to rotate correspondingly. This adjustment feature enables the orientation of the image being displayed to be changed. The movement of the digital camera duplicates the capability of conventional laparoscopes and endoscopes to vary the view, which is often used by surgeons to obtain a useful image of the surgical field. This movement of the digital camera is indicated by the arrow disposed on elongate member 50, adjacent to mounting bracket 46.

Mounting bracket 48 enables two different types of motion to be achieved. Mounting bracket 48 includes an adjustment knob 48a and a shaft 64 and substantially encloses elongate member 50. When adjustment knob 48a is loosened, mounting bracket 48 (and elongate member 50) pivots with respect to shaft 64. This motion, referred to as tilting, is indicated by the curved arrow disposed adjacent to mounting bracket 48.

Shaft 64 is inserted into an opening 62 formed in a support block 60. Housing 32 is preferably formed of a relatively lightweight plastic material. Support block 60 provides additional support to mounting bracket 48, is fixedly coupled with housing 32, and if desired, can be formed integral to housing 32. Preferably, an interference fit exists between shaft 64 and opening 62, such that when no force is applied to elongate member 50 (or simulated laparoscope handle 42), the elongate shaft remains fixed in its then current position, and when a modest amount of pressure is applied to either elongate member 50 or simulated laparoscope handle 42, shaft 64 (and mounting bracket 48 and elongate member 50) move relative to opening 62. This motion, referred to as panning, is indicated by the curved arrow disposed adjacent to shaft 64. It should be understood that support block 60 is not required if housing 32 alone is sufficient to provide the required support.

Figure 5:
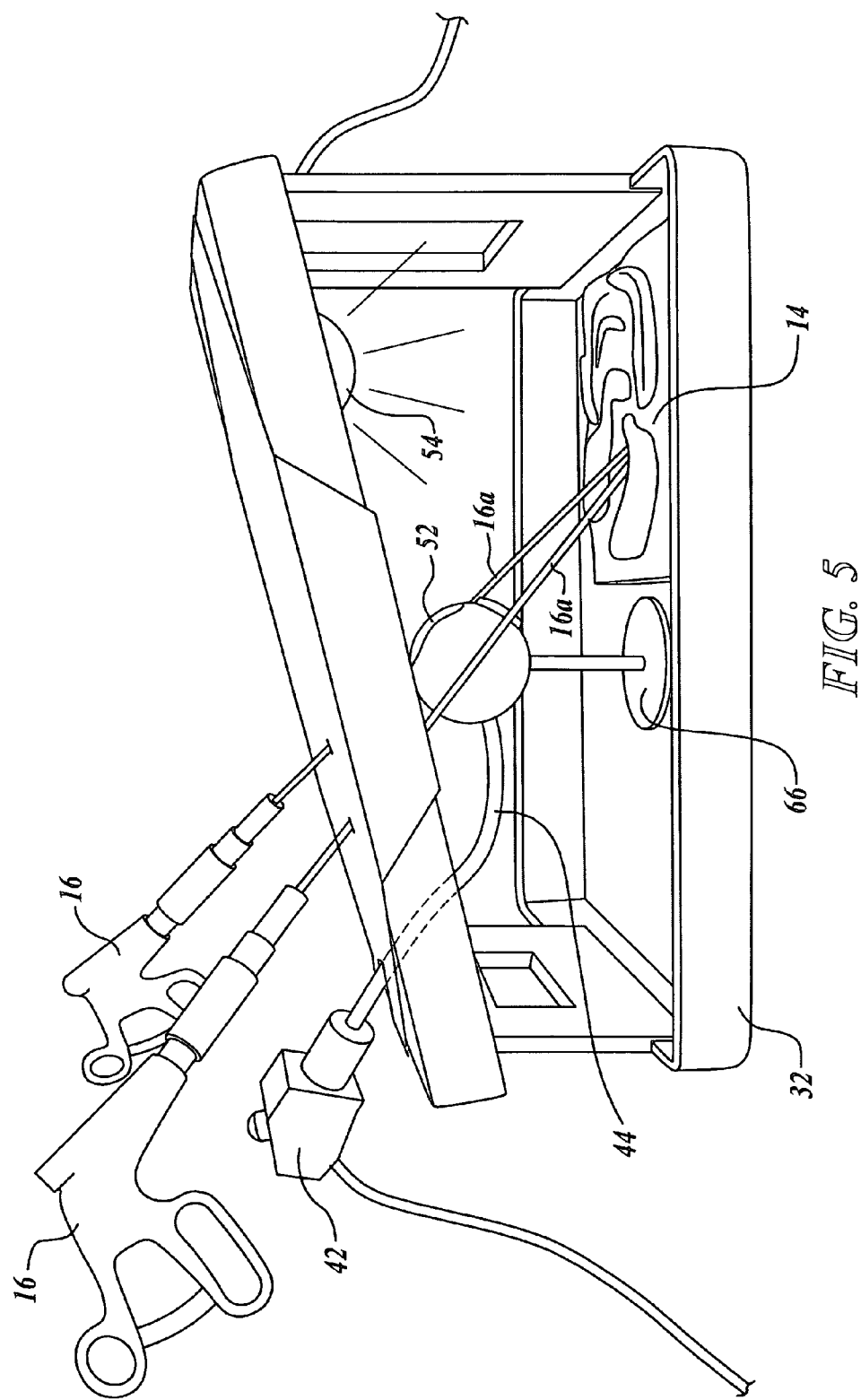
FIG. 5 is a side elevational view of a second embodiment of a surgical trainer including a digital camera disposed inside the trainer, in accord with the concepts disclosed herein.

FIG. 5 is a side view of an embodiment in which the digital camera is not moveably attached to a support. In this embodiment, digital camera 52 is attached to a fixed support 66. Support 66 is wholly enclosed within the practice volume defined by housing 32. Output line 44 from digital camera 52 is directed to simulated laparoscope handle 42. Optionally, a small portion of elongate member 50 can be included to simulate a laparoscope that is being used to enter a patient. It should be understood that simulated laparoscope handle 42 is not required in this embodiment or in the embodiments shown in the Figures discussed above. The purpose of simulated laparoscope handle 42 is to add realism to the simulation. In embodiments wherein the position of the digital camera is fixed, manipulation of simulated laparoscope handle 42 does not change the position of the digital camera.

Support 66 can be implemented in several different ways. For example, instead of the single shaft in a base as shown for support 66, a tripod support could be employed. In another embodiment, housing 32 is configured to be collapsible and portable. In such an embodiment, it is desirable for support 66 to include a hinge so that when support 66 is not in use, it can be folded substantially flat to enable housing 32 to be reduced in size for storage and transport purposes. Alternatively, support 66 can be removably coupled with the base of housing 32 to enable support 66 and digital camera 52 to be readily removed from the practice volume after use, so the trainer can be more compactly stored and transported.

Figure 6:
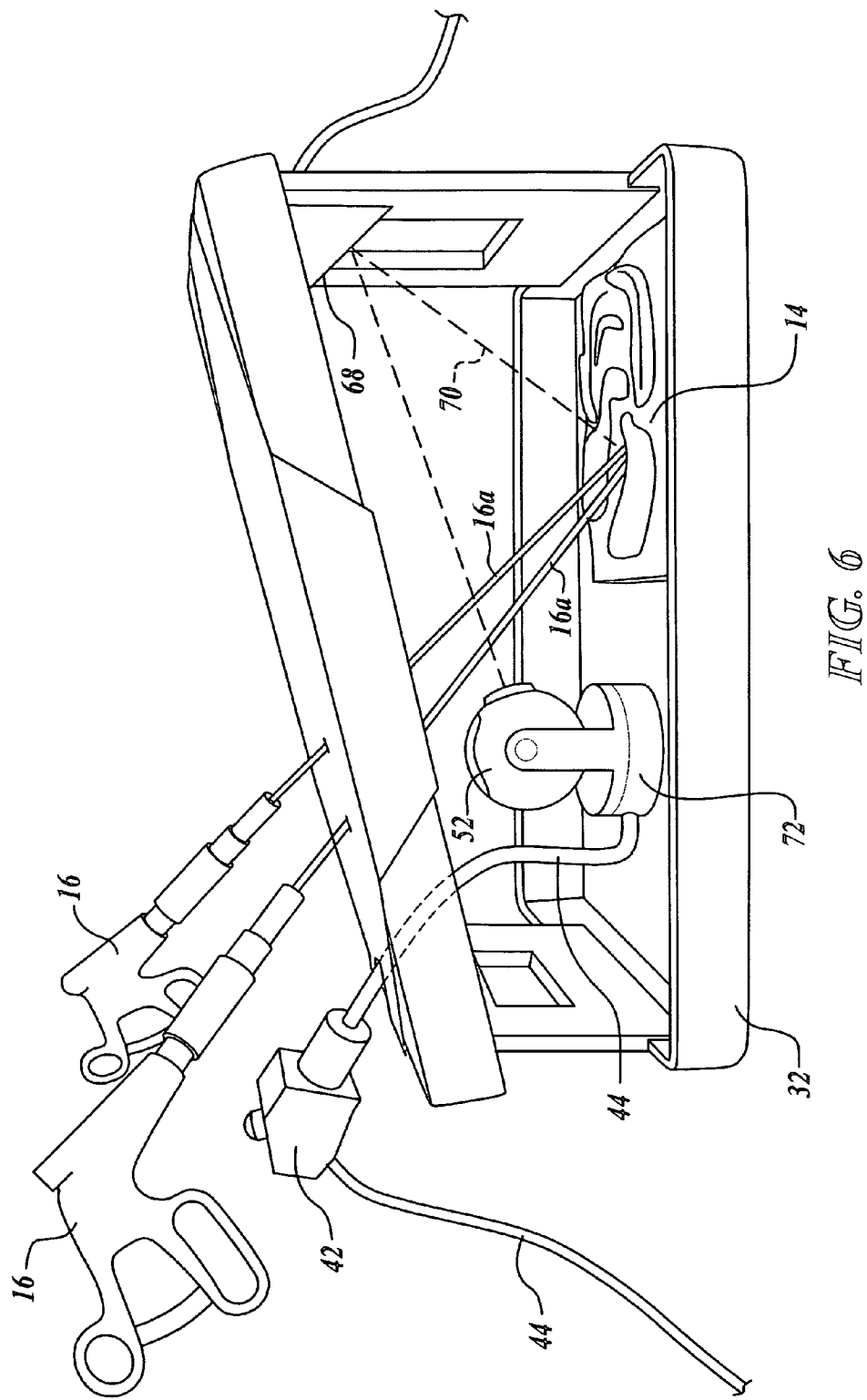
FIG. 6 is a side elevational view of yet another embodiment of a surgical trainer including a digital camera disposed inside the trainer.

FIG. 6 illustrates yet another embodiment in which digital camera 52 is attached to a mounting bracket 72 that is fully enclosed within housing 32. In this embodiment, the digital camera is disposed in a lower portion Of the practice volume defined by the housing. A reflector 68 is positioned so that digital camera 52 has a bird's eye view (i.e., a top view) of anatomical structure 14. A dash line indicates a light path 70 from anatomical structure 14 to digital camera 52. Each of digital camera 52, reflector 68, and anatomical structure 14 can be fixed in position. Alternatively, one or more of digital camera 52, reflector 68, and anatomical structure 14 can be movable within the practice volume defined by housing 42.

It should be understood that mounting brackets 48 and 46 described in regard to FIGS. 2-3 are exemplary of a configuration for movably supporting a digital camera. Those of ordinary skill in the art will recognize that many other configurations can be implemented for supporting either a digital camera or an elongate member to which a digital camera is mounted. For example, FIG. 7A illustrates a ball head mount 74 that can be used to support a digital camera. Ball head mount 74 includes a housing 82, a ball 76 enclosed within housing 82, and a plurality of adjustment levers 80. Digital camera 52 is attached to a support plate 78, which is attached to ball 76. When adjustment levers 80 are loosened, ball 76 is free to pivot about its center relative to housing 82, which enables digital camera 52 to be moved and positioned as desired. Ball mount 74 can be completely enclosed within housing 32 (as is support 66 of FIG. 5), so that ball mount 74 and digital camera 52 are not readily seen by a trainee.

FIG. 7B shows digital camera 52 that is attached to a pan and tilt head 84. Pan and tilt head 84 includes a support plate 86 and a plurality of adjustment controls 88. When adjustment controls 88 are loosened, the position of support plate 86 can be changed relative to orthogonal pan and tilt axes, as desired. Again, pan and tilt head 84 can be completely enclosed within housing 32.

FIG. 7C illustrates a ball head mount 74 used to support elongate member 50. Housing 82 is preferably disposed within housing 32, and support plate 78 is disposed outside of housing 32. Simulated laparoscope handle 42 is attached to support plate 78. When adjustment knobs 80 are loosened, the positions of simulated laparoscope handle 42, elongate member 50, and digital camera 52 can be changed as desired.

Although inexpensive digital cameras having limited functionality have been successfully used in a functional implementation of the concepts disclosed herein, consistent with system 30 of FIG. 2, more expensive digital cameras having greater functionality and image quality can certainly be employed in the alternative. The digital camera used in the working prototype is a QuickCam Messenger™ web camera available from Logitech Inc. of Fremont, Calif. The QuickCam Messenger™ is capable of a video capture resolution of up to 640×480 pixels, and a frame rate of up to 30 frames per second. The 30 frames per second rate is not comparable to broadcast television quality, yet still affords useful imagery. Lower frame rates result in a displayed image in which movements can appear "jerky." Higher frame rates can provide a smoother, higher quality image.

Higher cost digital cameras typically offer more functionality beyond simply providing more pixels and higher frame rates. For example, more expensive digital cameras often offer optical and/or digital zoom adjustment. While such zooming can be used to control the field of view obtained by a digital camera disposed within a trainer, the field of view obtained using a conventional laparoscope or endoscope is varied by physically repositioning the distal end of the scope and not by adjusting a zoom level of the lens/digital imaging system. Mounting brackets 46 and 48 as shown in FIG. 4 enable the digital camera to be moved within the practice volume, simulating motions used to change the field of view obtained by conventional laparoscopes and endoscopes. Thus, while some users may prefer digital and optical zoom adjustments in the feature set of the digital camera, such functionality is not required.

Another functionality available in more expensive digital cameras is a powered camera mount, which enables panning and tilting to be performed under remote control. X10 (USA) Inc. of Las Vegas, which produces a basic X10™ digital camera and also offers the Vanguard 44X™, a digital camera that provides pan, tilt, and optical and digital zooming—all under remote control. That digital camera is mounted to a base similar to the base shown in FIG. 6. The lower portion of the base rotates to enable panning, and the upper portion of the base (to which the camera is attached) controls tilt. As described above, while a less expensive digital camera movably coupled to a support enables the motion of conventional laparoscopes and endoscopes to be simulated, some users may desire the functionality of a digital camera that can pan and tilt in response to remote commands. For example, if system 30 of FIG. 2 is provided with both digital camera 52 coupled to elongate member 50, and a second digital camera that can be selectively positioned under remote control, an instructor could use the second digital camera to monitor a training exercise from a remote location. While the video signal from digital camera 52 (which provides the images displayed to the trainee) can also provide video images to an instructor at a remote location (by streaming the video signal over the Internet), the remote control digital camera enables the instructor to obtain a video signal and resulting images that are based on an angle and field of view selected by the instructor, not the trainee. If desired, a single, remotely controllable camera can be included in a trainer, in place of a fixed-position camera, or a digital camera coupled with an elongate support. In such an embodiment, a remote instructor can select a particular field of view within the practice volume, and instruct the trainee to perform some exercise at that location. If desired, such a remotely controllable camera can be under the trainee's control, such that the trainee can selectively pan, tilt, and/or zoom to obtain an image of a desired portion of the practice volume.

The use of a digital camera also enables many different training scenarios to be supported. The images can simply be displayed during a training exercise, so that the trainee is able to view their performance on the display, just as they would appear during a videoendoscopic procedure. In systems that include a computing device or are coupled to a tape deck or other recording medium, in addition to displaying the exercise in real-time, the image data can be stored for later review. This capability will be particularly useful to instructors who may not be present during the actual exercise, so that they can later review, with or without the trainee being present, the trainee's performance during the exercise. The image data can be streamed to observers over a computer network, such as the Internet. An instructor can thus broadcast an exemplary technique over such a network to students located in others locations. Instructors can also record training videos of exemplary techniques, to be distributed to students in an electronic format. Frames of video data that are particularly illustrative or interesting can be selected and individually printed or included in training materials.

FIG. 8 schematically shows an exemplary configuration 100 in which a training system 102 is connected to a network 104 to share video data of a training exercise with remote observers 106 and 108, and optionally a remote instructor 110. It should be understood that the number of observers connected to network 104 at any one time can readily vary. Training system 102 is based on system 30 of FIG. 2, and includes a computing device that is coupled to the network. Video data captured by the digital camera are both processed to drive a display in training system 102, as well as to provide video data streamed to other users over network 104, which can be a private network used by a school or training facility, or a public network, such as the Internet. As discussed above, the video data captured by the digital video camera can be stored in digital form, for example, on a hard drive (not separately shown) of the computing device of training system 102. If desired, the training system can also couple via network 104 to a remote storage device 112, to store the image data remotely. Such remote storage is particularly useful in a scholastic environment, where students share a plurality of different training systems 102, so that each training system stores training data at a common remote storage device. As described above, in some embodiments, trainers are equipped with a second digital camera disposed within the practice volume, enabling an instructor to control the field of view of the second digital camera independent of the digital camera displaying the image to the trainee using training system 102. In such an embodiment, the second digital camera can be motorized to enable pan and tilt to be remotely controlled. Instructor 110 is shown as optionally coupled to the trainer, since not all embodiments of the concepts disclosed herein include a second, remotely controlled digital camera.

FIG. 9A is a flow diagram 120 that generally shows the logic for using an endoscopic surgical skills trainer including a digital camera within the practice volume to enhance videoendoscopic skills training. In a block 122, an endoscopic surgical skills trainer including a digital camera within the practice volume is provided. Any of the trainers shown in FIG. 2, 3, 5, or 6 can be beneficially employed. In a block 124, an exercise object is introduced into the practice volume. The exercise object can be a simulated anatomical structure, or some other object that the trainee will manipulate during a training exercise. For example, as noted above, a plurality of rice grains can be employed as exercise objects. Even such simple objects can provide practical skills training. In a block 126, the digital camera is used to provide image data for display to the trainee on a video monitor, television, or other display. Optionally, a trainer can include a digital camera having a fixed position. In such an embodiment, care must be taken that the training object or objects are placed within the field of view obtainable with the fixed-position digital camera. In embodiments where the digital camera is movable and selectively repositionable, block 126 can include the step of moving the digital camera so that the exercise object is in the field of view obtained by the digital camera. In a block 128, the trainee performs the exercise while viewing the progress of the exercise on the display.

FIG. 9B highlights optional steps associated with block 128. In an optional block 130, the data used to drive the display monitored by the trainee are also stored for later review. In an optional block 132, the video data are also transmitted over a network connection to enable remote observers to watch the trainee's progress during the exercise.

In an exemplary implementation, the video camera is a web cam. Significantly, the video camera can be implemented using any imaging sensor configured to provide a signal that can be used to drive a video display, either directly, or after additional processing (for example, the additional processing can be provided by a computing device or hardware, such as an application specific integrated circuit (ASIC), not separately shown). Significantly, the imaging sensor does not need to be incorporated into a housing suitable for performing laparoscopic or endoscopic procedures. Thus, any housing enclosing the working components of the imaging sensor need not be small enough for use in vivo. Indeed, because the form factor for the imaging sensor is not critical in the context of the disclosure provided herein (as compared to form factors required for in vivo applications), low cost imaging sensors (such as ubiquitous web cams) can be employed. Note that coupling a web cam to a distal end of a boom or elongate support structure would be entirely unsuitable for in vivo applications. Conventional laparoscopes and endoscopes typically include optical fibers rather than imaging sensors, because the form factor of laparoscopic optical fibers are significantly smaller than the form factors of conventional imaging sensors. Coupling conventional imaging sensors to the end of an elongate support structure would result in a form factor too large for minimally invasive insertion into a body. Significantly, the optical fibers used in conventional laparoscopes and endoscopes are substantially encapsulated by a flexible elongate lumen configured for minimally invasive insertion into a body. In the exemplary embodiment described above, where a web cam is coupled to the distal end of an elongate support structure (see FIGS. 3 and 4 in particular), the elongate support structure does not envelop or encapsulate the web cam.

Yet another aspect of the concepts disclosed herein is a camera mounting bracket for coupling a digital camera to an elongate member, such that the camera mounting bracket includes a plurality of different positions for the digital camera. This configuration enables the same trainer to simulate endoscopes and laparoscopes, providing a variety of different viewing angles. Often, a lens or light collecting element at the distal end of endoscope or laparoscope is disposed at a zero degree angle relative to the generally elongate body of the endoscope (this configuration achieves what is referred to as a 0° viewing angle), viewing forward along the longitudinal axis of the endoscope. However, endoscopes and laparoscopes are available that provide a different viewing angle, by placing the lens or light collecting element at a different angle relative to the longitudinal axis of the generally elongate body of the endoscope. FIG. 10A schematically illustrates the distal portions of four different prior art endoscopes exhibiting optical viewing angles of 0°, 20°, 30°, and 45°. These optical angles can be readily achieved when the light collecting element is an optical fiber, simply by cutting the distal end of the optical fiber at the desired angle. With respect to the concepts disclosed herein, duplicating the different viewing angles with which clinicians are familiar is more problematical, because a digital camera is used in place of the optical fibers in conventional endoscopes and laparoscopes.

FIGS. 10B and 10C schematically illustrate camera mounting brackets that can be used to couple a digital camera to an elongate member, such that a plurality of different viewing angles can be achieved. The brackets illustrated in FIGS. 10B and 10C are particularly well-suited for use in the trainers of FIGS. 3 and 4, each of which include a digital camera coupled to a distal end of an elongate member.

The camera mounting bracket of FIG. 10B includes three different positions that can be used to attach the digital camera to the camera mounting bracket, which itself is securely attached to the distal end of the elongate member. The camera mounting bracket may be formed from a variety of different materials, such as metal or plastic. The size and shape of the camera mounting bracket are such that injection molding techniques can be readily used to produce the mounting brackets in quantity. A particularly preferred attachment can be achieved by forming a threaded opening into the digital camera, and providing a corresponding threaded shaft coupled to an adjustment knob. The bracket includes three different openings, each corresponding to one of three different mounting positions. The threaded shaft will be placed into the opening selected, and then into the threaded opening in the digital camera. The knob can be used to screw the threaded shaft into the threaded opening, thereby securing the digital camera to the camera mounting bracket. As indicated in FIG. 10B, such a threaded shaft and knob have been used to secure the digital camera using a first of the three different attachment positions. The first position (i.e., the opening that the threaded shaft and knob occupy in FIG. 10B) corresponds to a 0° viewing angle. The middle opening corresponds to a 30° viewing angle, while the final opening corresponds to a 45° viewing angle. Those of ordinary skill in the art will readily recognize that additional viewing angles can be achieved by forming differently disposed openings in other portions of the camera mounting bracket. Thus, while the camera mounting bracket of FIG. 10B includes three openings enabling three different mounting positions to be achieved, it should be understand that the specific number of different mounting positions achievable using such a camera mounting bracket can be varied by providing either more or fewer openings, and that three different mounting positions (achieving three different viewing angles) is simply exemplary, and is not intended to limit the concepts disclosed herein.

The camera mounting bracket of FIG. 10C includes only a single opening, forming a generally elongate channel in the camera mounting bracket spanning the distance between the first and third openings in the camera mounting bracket of FIG. 10B (i.e., the openings corresponding to the 0° and 45° viewing angles). A threaded shaft and knob are introduced into the single opening and used to secure the digital camera to the camera mounting bracket. Note that the camera mounting bracket of FIG. 10C is not limited to only three viewing angles, but is infinitely positionable between a minimum viewing angle (e.g., 0°) and a maximum viewing angle (e.g., 45°). Dots or markings can be formed into or applied on the camera mounting bracket to indicate the position of frequently used viewing angles, such as 45° or 30°. A graduated scale can be provided on the camera mounting bracket so that the clinician can determine what viewing angle is associated with the particular portion of the opening.

With respect to the use of threaded shaft and knob being used to securely attach a digital camera to the camera mounting bracket, it should be understood that such attachment mechanism is merely exemplary, and not intended to limit the concepts disclosed herein. Those of ordinary skill in the art will readily recognize that many other different mechanical configurations can be used to attach an item such as a digital camera to a camera mounting bracket.

FIGS. 11A and 11B are monochromatic images of a prototype multi-position camera bracket consistent with the camera mounting bracket of FIG. 10B, such that the digital camera is attached to the multi-position camera bracket using a first one of three different possible attachment positions (i.e. the 0° viewing angle).

FIGS. 11C and 11D are monochromatic images of the prototype multi-position camera bracket of FIGS. 10B, 11A, and 11B, such that the digital camera is attached to the multi-position camera bracket using a second one of three different possible attachment positions (i.e. the 30° viewing angle).

FIG. 11E is a monochromatic image of the prototype multi-position camera bracket of FIGS. 10B and 11A-11D, configured such that the digital camera is attached to the multi-position camera bracket using a third one of three different possible attachment positions (i.e. the 45° viewing angle).

With respect to the prototype camera mounting bracket, empirical testing was performed to determine where the openings needed to be formed on the camera mounting bracket to achieve the desired viewing angles (i.e., the 0° angle, the 30° angle, and the 45° angle). Similar empirical studies can be performed to determine the positions required to achieve other viewing angles. For example, 15° viewing angles, 35° viewing angles, and 70° viewing angles are known and the opening positions to achieve these angles might also be empirically determined. It should be understood that the concepts disclosed herein are not limited to any specific viewing angle.

It should also be recognized that the camera mounting bracket can be implemented in surgical trainers that do not also implement the elongate support structure or boom. For example, camera mounting brackets generally consistent with those described above can be incorporated into the surgical trainer schematically illustrated in FIG. 5, to enable additional viewing angles to be achieved (i.e., it camera mounting bracket disclosed above can be attached to fixed support 66). Furthermore, it should be recognized that the camera mounting bracket could be attached directly to the housing (i.e., the camera mounting bracket could be used in place of fixed support 66).

The camera mounting brackets disclosed herein enable different viewing angles to be achieved by enabling a position of a digital video camera to be changed relative to the camera mounting bracket within the volume of the surgical trainer. In some embodiments, substantially the entire digital video camera is moved relative to the camera mounting bracket. It should be recognized however, that the change in viewing angles is primarily achieved by moving the digital video camera optics responsible for collecting light relative to the camera mounting bracket, so that the camera orientation and the direction in which it acquires an image are changed.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A videoendoscopic surgery trainer for practicing videoendoscopic or videolaparoscopic surgical techniques, comprising:
    (a) a housing defining a practice volume; and
    (b) a simulated laparoscope comprising:
        (i) a handle having a size and shape simulating a handle of a medical laparoscope;
        (ii) a hollow elongate member extending from a distal portion of the handle into the practice volume;
        (iii) a digital video camera configured to obtain an image of at least a portion of the practice volume and to output a corresponding signal that can be used to generate a video signal to drive a display;
        (iv) a digital video camera mounting bracket coupled to a distal end of the hollow elongate member, the digital video camera being physically attached to the digital video camera mounting bracket, thereby supporting the digital video camera within the practice volume, the digital video camera mounting bracket being configured to enable a position of the digital video camera relative to the digital video camera mounting bracket to be selectively changed, thereby enabling the digital video camera to achieve a plurality of different viewing angles by either manually changing a position of a proximal end of the elongate member or by changing the position of the digital video camera relative to the a digital video camera mounting bracket; and
        (v) a data cable having a proximal end and a distal end, the distal end being logically coupled to the digital video camera, the proximal end being configured to logically couple to at least one of a display and a computing device, a first portion of the data cable extending from the digital video camera and the handle being disposed inside the elongate member, a second portion of the data cable extending from the handle to the proximal end of the data cable, the second portion of the data cable extending outwardly and away from a proximal portion of the handle, the data cable being configured to be coupled to a computing device.

2. The trainer of claim 1, wherein the digital video camera mounting bracket does not substantially envelop the digital video camera.

3. The trainer of claim 1, wherein the digital video camera mounting bracket is configured to enable at least two of the following viewing angles to be achieved:
    (a) 0°;
    (b) 20°;
    (c) 30°; and
    (d) 45°.

4. The trainer of claim 1, wherein the digital video camera mounting bracket comprises at least one of:
    (a) a ball mount;
    (b) a pan and tilt head; and
    (c) a motorized support enabling powered positioning of the digital video camera to be achieved.

5. The trainer of claim 1, wherein the digital video camera mounting bracket comprises a plurality of different attachment points for coupling with the digital video camera, each different attachment point enabling the digital video camera to achieve a different viewing angle.

6. The trainer of claim 5, wherein each attachment point comprises an opening configured to receive a threaded shaft, the threaded shaft passing through a selected opening and engaging a threaded opening in the digital video camera, thereby coupling the digital video camera to the digital video camera mounting bracket, adjustment of the viewing angle being achieved by selecting a different opening for receiving the threaded shaft.

7. The trainer of claim 1, wherein the digital video camera mounting bracket comprises a single adjustable attachment point for coupling with the digital video camera, the single attachment point enabling adjustable mounting of the digital video camera, thereby enabling the digital video camera to achieve a plurality of different viewing angles.

8. The trainer of claim 7, wherein the attachment point comprises an elongate opening configured to receive a threaded shaft, the threaded shaft passing through the elongate opening and engaging a threaded opening in the digital video camera, thereby coupling the digital video camera to the digital video camera mounting bracket, adjustment of the viewing angle being achieved by moving the threaded shaft within the elongate opening.

9. A videoendoscopic surgery trainer for the practice of videoendoscopic or laparoscopic surgery techniques, the trainer comprising:
(a) a housing defining a practice volume;
(b) a digital imaging sensor disposed within the practice volume, the digital imaging sensor being configured to capture a plurality of frames per second, such that the digital imaging sensor can provide a digital video feed of at least a portion of the practice volume, the digital imaging sensor comprising a curved housing;
(c) a support structure comprising an elongate member, the elongate member having a proximal end disposed outside of the practice volume, and a distal end disposed inside the practice volume, the digital imaging sensor being disposed proximate to the distal end of the elongate member, so that manipulating a position of the proximal end of the elongate member results in a change in a position of the digital imaging sensor within the practice volume; and
(d) a digital imaging sensor mounting bracket configured to couple with the digital imaging sensor and the distal end of the elongate member, thereby supporting the digital imaging sensor within the practice volume, the digital imaging sensor mounting bracket being configured to enable a position of the digital imaging sensor relative to the digital imaging sensor mounting bracket to be selectively changed, thereby enabling the digital imaging sensor to provide a plurality of different viewing angles, the digital imaging sensor mounting bracket comprising an curved surface to supportingly engage the curved housing of the digital imaging sensor.

10. The trainer of claim 9, wherein the digital imaging sensor mounting bracket is configured to enable at least two of the following viewing angles to be achieved:
(a) 0°;
(b) 20°;
(c) 30°; and
(d) 45°.

11. The trainer of claim 10, wherein the digital imaging sensor mounting bracket comprises a plurality of different attachment points for coupling with the digital imaging sensor, each different attachment point enabling the digital imaging sensor to be mounted so as to achieve one of the viewing angles defined in claim 10.

12. The trainer of claim 11, wherein each different attachment point comprises an opening configured to receive a threaded shaft, the threaded shaft passing through a selected opening and engaging a threaded opening in the digital imaging sensor, thereby coupling the digital imaging sensor to the digital imaging sensor mounting bracket, adjustment of the viewing angle being achieved by selecting a different opening for receiving the threaded shaft, each opening being located on a different portion of the curved surface.

13. The trainer of claim 9, wherein the digital imaging sensor mounting bracket comprises a single adjustable attachment point for coupling with the digital imaging sensor, the single adjustable attachment point being selectively coupled with the digital imaging sensor so as to achieve a plurality of different viewing angles.

14. The trainer of claim 13, wherein the attachment point comprises an elongate opening configured to receive a threaded shaft, the threaded shaft passing through the elongate opening and engaging a threaded opening in the digital imaging sensor, thereby coupling the digital imaging sensor to the digital imaging sensor mounting bracket, adjustment of the viewing angle being achieved by moving the threaded shaft within the elongate opening, the elongate opening extending along the curved surface, along a longitudinal axis of the digital imaging sensor bracket.

15. The trainer of claim 9, wherein the digital imaging sensor mounting bracket comprises markings generally indicating what viewing angle will be achieved when the position of the digital imaging sensor relative to the digital imaging sensor mounting bracket is selectively changed.

16. The trainer of claim 9, wherein the digital imaging sensor comprises a web cam.

17. A method for simulating an internal imaging of an endoscopic or laparoscopic procedure, comprising the steps of:
(a) providing a surgical trainer that defines a practice volume in which a simulated endoscopic or laparoscopic procedure can be performed upon at least one exercise object, the surgical trainer including a simulated laparoscope comprising:
(i) a handle having a size and shape simulating a medical laparoscope;
(ii) an elongate member extending from a distal portion of the handle into the practice volume;
(iii) a digital imaging sensor coupled to a distal end of the elongate member and disposed within the practice volume, the digital imaging sensor producing a digital video signal conveying images of at least a portion of the practice volume; and
(iv) a data cable having a proximal end and a distal end, the distal end being logically coupled to the digital imaging sensor, the proximal end being configured to logically couple to at least one of a display and a computing device, a first portion of the data cable extending between a location inside the practice volume proximate the digital imaging sensor and the handle being disposed inside the elongate member, a second portion of the data cable extending from the handle to the proximal end of the data cable, the second portion of the data cable extending outwardly and away from a proximal portion of the handle, the data cable being configured to be coupled to a computing device;
(b) producing a signal conveying images of the at least one exercise object from a first viewing angle using the digital imaging sensor disposed within the practice volume while the digital imaging sensor is coupled to a support structure at a first one of a plurality of attachment points, each one of the support structure's different attachment points causing the digital imaging sensor to acquire an image of the practice volume using a different predefined viewing angle, the support structure being coupled to a distal end of the elongate member;
(c) displaying the images of the at least one exercise object conveyed by the signal in regard to the first viewing angle while the digital imaging sensor is coupled to the support structure at the first attachment point;
(d) manipulating an orientation of the digital imaging sensor relative to the support structure such that the digital imaging sensor is coupled to the support structure using a different one of the plurality of attachment points, thereby causing the digital imaging sensor to acquire an image of the practice volume using a different one of the predefined viewing angles; and
(e) displaying the images of the at least one exercise object conveyed by the signal, in regard to a second viewing angle while the digital imaging sensor is coupled to the support structure at the second attachment point.

18. The method of claim 17, wherein the step of manipulating the orientation of the digital imaging sensor relative to the support structure comprises the step of selecting an attachment point configured to enable one of the following predefined viewing angles to be achieved:
 (a) 0°;
 (b) 20°;
 (c) 30°; and
 (d) 45°.

19. A method for changing a viewing angle provided by a simulation of an internal imaging of an endoscopic or laparoscopic procedure, comprising the steps of:
 (a) producing a signal conveying images of the simulation of the internal imaging of the endoscopic or laparoscopic procedure from a first viewing angle using a digital video camera disposed within a practice volume;
 (b) displaying the images of the simulation of the internal imaging of the endoscopic procedure conveyed by the signal in regard to the first viewing angle;
 (c) manipulating a support structure that movably supports the digital video camera, thereby selectively changing a position of the digital video camera relative to the support structure, so that the digital video camera produces a signal conveying images of the simulation of the internal imaging of the endoscopic or laparoscopic procedure from a second viewing angle, the support structure comprising a curved surface that supportingly engages an curved housing of the digital video camera, wherein the step of manipulating the support structure comprises at least one of the steps of:
  (i) repositioning a threaded fastener that couples the digital video camera to the digital video camera mounting bracket, from a opening in the digital video camera mounting bracket that was used to achieve the first viewing angle, so that the threaded fastener couples the digital video camera to the digital video camera mounting bracket in a different opening, and thereby achieves the second viewing angle; and
  (ii) sliding the threaded fastener with an elongate opening in the support structure so that the digital video camera is coupled to the digital video camera mounting bracket in a different position, to achieve the second viewing angle; and
 (d) displaying the images of the simulation of the internal imaging of the endoscopic procedure conveyed by the signal, in regard to the second viewing angle.

20. A videoendoscopic surgery trainer for practicing videoendoscopic or videolaparoscopic surgical techniques, comprising:
 (a) a housing defining a practice volume;
 (b) a digital video camera disposed within the practice volume, the digital video camera producing a digital video signal conveying images of at least a portion of the practice volume;
 (c) an elongate member having a proximal end disposed outside of the practice volume, and a distal end disposed inside the practice volume, the digital video camera being disposed proximate to the distal end of the elongate member, so that manipulating a position of the proximal end of the elongate member results in a change in a position of the digital video camera within the practice volume; and
 (d) a digital video camera mounting bracket coupled to the distal end of the elongate member, the digital video camera being attached to the digital video camera mounting bracket, the digital video camera mounting bracket being configured to enable a position of the digital video camera relative to the digital video camera mounting bracket to be selectively changed, thereby enabling the digital video camera to achieve a plurality of different viewing angles, without requiring the elongate member to be repositioned.

21. A method for changing a viewing angle provided by a simulation of an internal imaging of an endoscopic or laparoscopic procedure, comprising the steps of:
 (a) producing a signal conveying images of the simulation of the internal imaging of the endoscopic or laparoscopic procedure from a first viewing angle using a digital video camera disposed within a practice volume;
 (b) manipulating a first support structure to selectively change a position of a digital video camera inside a practice volume, until the digital video camera acquires first image data from a desired portion of the practice volume, the first image data corresponding to images acquired using a first viewing angle; and
 (c) without manipulating the first support structure, manipulating a second support structure until the digital video camera acquires second image data from the desired portion of the practice volume, the second image data corresponding to images acquired using a second viewing angle.

* * * * *